(12) United States Patent
Hawkins et al.

(10) Patent No.: US 6,716,971 B1
(45) Date of Patent: Apr. 6, 2004

(54) PTERIDINE NUCLEOTIDE ANALOGS

(75) Inventors: Mary E. Hawkins, Potomac, MD (US); Wolfgang Pfleiderer, Konstanz (DE); Frank Balis, Bethesda, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/786,666
(22) PCT Filed: Sep. 7, 1999
(86) PCT No.: PCT/US99/20541
§ 371 (c)(1), (2), (4) Date: May 15, 2001
(87) PCT Pub. No.: WO00/14101
PCT Pub. Date: Mar. 16, 2000

Related U.S. Application Data
(60) Provisional application No. 60/099,487, filed on Sep. 8, 1998.

(51) Int. Cl.$^7$ .................. C07H 21/00; C07H 21/02; C07H 21/04; C12Q 1/68
(52) U.S. Cl. .................. 536/23.1; 536/24.3; 536/25.3; 536/26.6; 435/6
(58) Field of Search ............ 435/6; 526/23.1, 526/24.3, 25.3, 26.6

(56) References Cited

U.S. PATENT DOCUMENTS 6,451,530 B1 * 9/2002 Hawkins .................. 435/6

FOREIGN PATENT DOCUMENTS

| WO | WO95/31469 | 11/1995 |
| WO | WO98/26093 | 6/1998 |

OTHER PUBLICATIONS

Jungmann et al., "Pteridine Nucleosides Analogs of 2'-Deoxyadenosine as Building Blocks for Oligonucleotide Synthesis," *Nucleosides & Nucleotides*, 16:5 & 6, (1997), pp. 863–868.

Taylor et al.; "Condensation of Phosphonate Anions with 4–Amino–5–nitrosopyrimidines: a New Pteridine Synthesis," *Chemical Communications* (Feb., 1971), p. 189.

Hawkins et al., "Fluorescence Properties of Pteridine Nucleoside Analogs as Monomers and Incorporated into Oligonucleotides," *Analytical Biochemistry* 244, pp. 86–95 (1997).

* cited by examiner

Primary Examiner—Jezia Riley
(74) Attorney, Agent, or Firm—Townsend and Townsend and Crew LLP

(57) ABSTRACT

The invention provides pteridine nucleotides of formula (I) which are highly fluorescent and which can be used in the chemical synthesis of fluorescent oligonucleotide. The invention further provides for fluorescent oligonucleotide comprising one or more pteridine nucleotides. In addition the invention provides for pteridine nucleotide triphosphates which may be used as the constituent monomers in DNA amplification procedures. The pteridine nucleotides are more stable and possess higher quantum yields than structurally similar pteridine nucleotides.

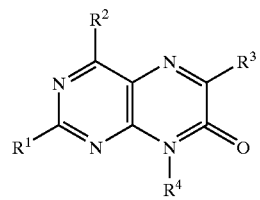

(I)

30 Claims, 6 Drawing Sheets

PTERIDINE NUCLEOTIDE ANALOGS

RELATED APPLICATIONS

The application claims priority to U. S. Provisional Patent Application No. 60/099,487 filed Sept. 8, 1998, the teachings of which are incorporated herein by reference in their entirety for all purposes.

BACKGROUND OF THE INVENTION

Fluorescence is a useful analytical technique for studying nucleic acid/nucleic acid and protein/nucleic acid interactions. In particular, fluorescent nucleosides and their analogs can be used to probe the physical and chemical environment of macromolecules to which they are covalently bonded or electrostatically attached. Various physical and chemical environmental changes can be assessed using fluorescence such as, changes in pH, interaction with other molecules, or alteration in tertiary structure. These changes can manifest differences in fluorescence intensity, the lifetime of fluorescence emission or fluorescence depolarization. In addition, there can be a shift in the emission, excitation, or absorption spectra of the fluorescent nucleoside depending on its environment. By measuring changes in fluorescence, useful information relating to macromolecule interactions, nucleic acid hybridization and enzymatic reactions can be obtained.

Fluorescent oligonucleotides find additional uses in molecular biology as probes for screening genomic and complementary DNA libraries, as primers for DNA synthesis, sequencing, and amplification reactions. Oligonucleotide probes have also proven useful for assaying in vitro gene expression using techniques of in situ hybridization. Recent improvements in DNA sequencing methods, fluorescent labels, and detection systems have dramatically increased the use of fluorescently labeled oligonucleotides in all of the foregoing applications. Typically, oligonucleotides are labeled with a fluorescent marker, either directly through a covalent linkage (e.g., a carbon linker), intercalation, or indirectly whereby the oligonucleotide is bound to a molecule such as biotin or dioxigenin, which is subsequently coupled to a fluorescently labeled binding moiety (e.g., streptavidin or a labeled monoclonal antibody).

These fluorescent labeling systems, however, suffer the disadvantage that the fluorescent complexes and their binding moieties are relatively large. The presence of large fluorescent labels and associated linkers can alter the mobility of the oligonucleotide, either through a gel as in sequencing, or through various compartments of a cell. Also, the means of attachment, typically through a 6-carbon linker, positions the probe at some distance from the other bases and allows movement of the probe in ways unrelated to the movement of the oligonucleotide. This can distort fluorescent depolarization measurements.

Ideally, a fluorescent nucleoside analog should closely resemble the naturally occurring purine or pyrimidine base structure. In particular, the probe should be attached to the oligonucleotide through the native deoxyribose chain. This keeps the probe aligned with other bases in the oligonucleotide and allows it to move in a more native-like manner. The analog should especially possess similar hydrogen bonding interactions. One type of nucleoside analog is a furanosyl pteridine derivative. Pteridines are a class of bicyclic planar compounds, some of which are highly fluorescent and are structurally similar to purines (see, FIG. 1). In fact, the fluorescence of many pteridine nucleoside analogs is known. U.S. Pat. No. 5,525,711, herein incorporated by reference, discloses pteridine nucleotide analogs as fluorescent DNA probes.

SUMMARY OF THE INVENTION

The present invention provides fluorescent nucleoside analogs that closely resemble the naturally occurring purine base structure These pteridine nucleotides are much more stable and possess higher quantum yields than prior art compounds. As such, the present invention provides pteridine nucleotides of Formula I:

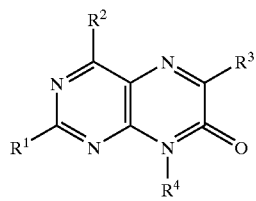

I

In Formula I, $R^1$ is a functional group including, but not limited to, hydrogen and optionally substituted $C_1$–$C_6$-alkyl.

In Formula I, $R^2$ is a functional group including, but not limited to, amino and mono- or di-substituted amino wherein the substituent(s) is a protecting group.

In Formula I, $R^3$ is a functional group including, but not limited to, optionally substituted $C_1$–$C_6$-alkyl.

In Formula I, $R^4$ is a functional group including, but not limited to, hydrogen and a compound having formula L.

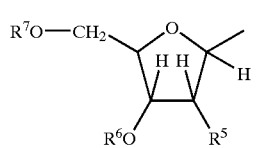

L

In Formula L, $R^5$ is a functional group including, but not limited to, hydrogen, hydroxyl and substituted hydroxyl wherein the substituent is a protecting group.

In Formula L, $R^6$ is a functional group including, but not limited to, hydrogen, phosphoramidite, an H-phosphonate, a methyl phosphonate, a phosphorothioate, a phosphotriester, a hemisuccinate, a hemisuccinate covalently bound to a solid support, a dicyclohexylcarbodiimide, and a dicyclohexylcarbodiimide covalently bound to a solid support.

In Formula L, $R^7$ is a functional group including, but not limited to, hydrogen, a phosphate, a triphosphate, and a protecting group. In addition, $R^1$ and $R^4$ are not simultaneously L.

Compounds of Formula I are highly fluorescent under normal physiological conditions, and suitable for use in the chemical synthesis of oligonucleotides.

In another embodiment, the present invention relates to oligonucleotides that incorporate these pteridine nucleotides.

In yet another embodiment, the present invention relates to pteridine nucleotide triphosphates that may be utilized in various nucleic acid amplification processes. When used in a nucleic acid amplification process, the pteridine nucleotide triphosphates are directly incorporated into the amplified sequence rendering it fluorescent.

In still yet another embodiment, this invention relates to methods of detecting the presence, absence, or quantity of a target nucleic acid. The methods involve probing the target nucleic acid with a nucleic acid probe identical in sequence to the target sequence with the addition of the pteridine probe that does not have a pairing partner. When annealing occurs, the pteridine probe is squeezed out of the base stacking into a loop. This removes the pteridine probe from the quenching effects of base stacking and yields an increase in fluorescence intensity.

In one preferred embodiment, the loop in the above probe ranges in length from about 1 to about 100 nucleolides when the probe hybridizes to the target nucleic acid. In particularly preferred probes, the loop is an insertion in the nucleic acid probe that is otherwise complementary to the target nucleic acid or to a contiguous subsequence of the target nucleic acid. In some preferred embodiments, the insertion is three nucleotides in length and which two nucleotides are each adjacent to the fluorescent nucleotide. In particularly preferred embodiments, at least one nucleotide adjacent to the fluorescent nucleotide is a purine (e.g., adenosine), and in still more preferred embodiments, the fluorescent nucleotide is bordered by at least two adjacent purines (e.g., adenosine) in both the 5' and 3' direction. In a most preferred embodiment, the insertion is a single base insertion; a pteridine nucleotide of Formula I.

In yet another embodiment, the insertion is self-complementary and forms a hairpin in which the fluorescent pteridine nucleotide is present in the loop of the hairpin and does not participate in complementary base pairing. The nucleotides comprising the loop can be selected such that they are not complementary to the corresponding nucleotides of the target nucleic acid when the probe is hybridized to the target nucleic acid and where the probe is complementary to at least two non-contiguous subsequences of the target nucleic acid.

In still yet another embodiment, the invention also provides kits for performing nucleic acid amplifications or for detecting the presence absence or quantity of a nucleic acid in a sample. The kits comprise a container containing any of the probes or label oligonucleotide having a compound of Formula I described herein. The kit can further comprise, a buffer, and/or any of the other reagents useful for practicing the method to which the kit is directed. These and other embodiments of the present invention will be described in detail below.

DETAILED DESCRIPTION OF THE INVENTION

1. Glossary

Figure 1:
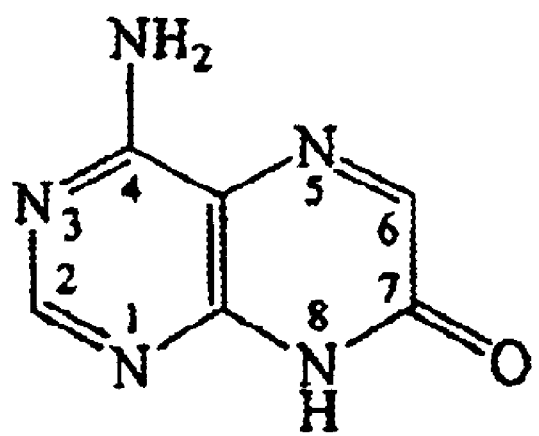
FIG. 1 illustrates the numbering system of a pteridine molecule.

The term "$C_1$–$C_6$-alkyl" denotes branched or unbranched hydrocarbon chains, such as, methyl, ethyl, n-propyl, iso-propyl, n-butyl, sec-butyl, iso-butyl, tert-butyl, octa-decyl and 2-methylpentyl. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoromethyl, 3-hydroxyhexyl, 2-carboxypropyl, 2-fluoroethyl, carboxymethyl, cyanobutyl and the like.

The term "oligonucleotide" refers to a molecule comprised of two or more deoxyribonucleotides, ribonucleotides, modified ribonucleotides, modified deoxyribonucleotides, ribonucleotide analogs, deoxyribonucleotide analogs, peptide nucleic acids, pteridine derivatives of the present invention, and other chemically modified nucleic acids. The exact size of an oligonucleotide depends on many factors and the ultimate function or use of the oligonucleotide. Generally, chemically synthesized oligonucleotides range in length from 2 to 500 bases, although, it is well known that oligonucleotides may be ligated together to provide longer sequences. As used herein, the term "oligonucleotide" also encompasses these longer sequences. It is also recognized that double-stranded polynucleotides may be created by hybridization with a complementary sequence or enzymatically through primer extension. The term oligonucleotide as used in this application encompasses both single and double-stranded oligonucleotide.

The term "solid support" refers to a solid material that is functionalized to permit the coupling of a monomer used in, polynucleotide synthesis. The solid support is typically coupled to a nucleoside monomer through a covalent linkage to the 3'-carbon on the furanose. Solid support materials typically are unreactive during the polynucleotide synthesis and simply provide a substratum to anchor the growing polynucleotide. Solid support materials include, but are not limited to, polacryloylmorpholide, silica, controlled pore glass (CPG), polystyrene, polystyrene/latex, and carboxyl modified Teflon.

The term "cleavage" in reference to solid phase oligonucleotide synthesis refers to the breaking of the bond that binds an oligonucleotide to a solid support. Typically, cleavage involves hydrolysis of a succinate ester bond between the 3'-hydroxyl of an attached oligonucleotide and the solid support.

The term "pteridine nucleotide" or "pteridine monomer" is used herein to refer to the furanosyl pteridine derivatives of the present invention with a 3'-phosphate group. It is recognized that properly speaking the furanosyl pteridine derivatives are not nucleotides as the pteridine is neither a purine nor a pyrimidine. However, because the furanosyl pteridine derivatives are structurally analogous to purine nucleotides, and the furanosyl pteridines of this invention are used in the same manner as nucleotides both will be referred to as nucleotides. As used herein, the pteridine nucleotide or pteridine monomer may be fully protected for use in polynucleotide synthesis or it may be deprotected when used as a triphosphate or when incorporated into an oligonucleotide.

The term "nucleotide monomer" as used herein refers to pteridine nucleotides, the "standard" nucleotides; adenosine, guanosine, cytidine, thymidine, and uracil, or derivatives of these nucleotides. Such derivatives include, but are not limited to, inosine, 5-bromodeoxycytidine, 5-bromodeoxyuridine, $N^6$-methyl-deoxyadenosine and 5-methyl-deoxycytidine.

As used herein, the term "protecting group" refers to a group that is joined to or substituted for a reactive group (e.g., a hydroxyl or an amine) on a molecule. The protecting group is chosen to prevent reaction of the particular radical during one or more steps of a chemical reaction. Generally the particular protecting group is chosen so as to permit removal at a later time to restore the reactive group without altering other reactive groups present in the molecule. The choice of a protecting group is a function of the particular radical to be protected and the compounds to which it will be exposed. The selection of protecting groups is well known to those of skill in the art. See, for example Greene et al., *Protective Groups in Organic Synthesis*, 2nd ed., John Wiley & Sons, Inc. Somerset, N.J. (1991).

As used herein, the term "protected amine" refers to an amine that has been reacted with an amino protecting group. An amino protecting group prevents reaction of the amide function during either the synthesis of the derivatized pteridine nucleoside or during the chemical synthesis of DNA or RNA using that nucleotide. The amino protecting group can be removed at a later time to restore the amino group without altering other reactive groups present in the molecule. For example, the exocyclic amine may be reacted with dimethylformamide diethylacetal to form the dimethylaminomethylenamino function. Amino protecting groups generally include carbamates, benzyl radicals, imidates, and others known to those of skill in the art. Preferred amino protecting groups include, but are not limited to, p-nitrophenylethoxycarbonyl or dimethyaminomethylenamino.

The term "coupling" is generally used in DNA synthesis to refer to the joining of one nucleotide monomer to another nucleotide monomer or to the 5' terminal of an oligonucleotide. The coupling is generally accomplished by the formation of a phosphodiester linkage from the 3'-phosphate of one nucleotide monomer to the 5'-hydroxyl of a second monomer or oligonucleotide. Coupling is also used to refer to the joining of an initial nucleoside to a solid support.

The term "label oligonucleotide", as used herein, refers to an oligonucleotide incorporating one or more fluorescent nucleotide analogues. The fluorescence activity of the nucleotide analogue(s) can be quenched partially or to a non-detectable level when the label oligonucleotide achieves a substantially linear conformation (i.e., the constituent bases, more particularly the fluorescent nucleotide(s), participate in normal base stacking). Preferred label oligonucleotide of this invention are capable of achieving a conformation, when hybridized to themselves or another nucleic acid or when bound by a nucleic acid binding protein, in which the quench (reduction of fluorescence intensity of the fluorescent nucleotide(s)) is diminished or eliminated resulting in a label oligonucleotide having increased fluorescence when present in that conformation. The label oligonucleotides of this invention are distinguished from labeled oligonucleotides wherein a label is attached. The labeled oligonucleotide can of course be attached to (labeled with) a label oligonucleotide of the present invention either directly through a phosphodiester linkage or indirectly through a linker.

The terms "target nucleic acid" or "target oligonucleotide" refer to the nucleic acid sequence or nucleic acid subsequence that is to be detected using one or more label oligonucleotide of this invention. The label oligonucleotides typically hybridize to all or a part of the target nucleic acid under stringent conditions.

The term "corresponding nucleotide", is used to refer to the position of a nucleotide in a first nucleic acid by reference to a second nucleic acid. Thus, a corresponding nucleotide refers to a nucleotide that it is positionally located opposite to a base where neighboring bases are all hybridized pairs.

The term "probe" refers to the nucleic acid sequence or nucleic acid subsequence that is used to detect a target nucleic acid. In an especially preferred embodiment, a probe is a label oligonucleotide of this invention.

"Subsequence" refers to a sequence of nucleic acids that comprise a part of a longer sequence of nucleic acids.

Hybridization refers to the specific binding of two nucleic acids through complementary base pairing. Hybridization typically involves the formation of hydrogen bonds between nucleotides in one nucleic acid and their corresponding nucleotides in the second nucleic acid.

"Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

The phrase "hybridizing specifically to", refers to the binding, duplexing, or hybridizing of a molecule only to a particular nucleotide sequence or subsequence under stringent conditions when that sequence is present in a complex mixture (e.g., total cellular DNA or RNA).

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is at most about 0.01 to 1.0 M Na ion concentration (or other salts) at pH 7.0 to 8.3 and the temperature is at least about 30° C. for short probes (e.g., 10 to 50 nucleotides). Stringent conditions may also be achieved with the addition of destabilizing agents such as formamide.

The term complementary base pair refers to a pair of bases (nucleotides) each in a separate nucleic acid in which each base of the pair is hydrogen bonded to the other. A "classical" (Watson-Crick) base pair always contains one purine and one pyrimidine, adenine pairs specifically with thymine (A-T), guanine with cytosine (G-C), uracil with adenine (U-A). The two bases in a classical base pair are said to be complementary to each other.

A "nucleic acid amplification mixture" refers to the reaction mixture used to amplify a nucleic acid. The amplification may be by any method including but not limited to PCR, long range PCR, ligase chain reaction, self-sustained sequence replication, and the like. Typical nucleic acid amplification mixtures (e.g., PCR reaction mixture) include a nucleic acid template that is to be amplified, a nucleic acid polymerase, nucleic acid primer sequence(s), and nucleotide triphosphates, and a buffer containing all of the ion species required for the amplification reaction.

II. Fluorescent Nucleosides

In certain aspects, the compounds of this invention are fluorescent nucleosides that can be used in a great variety of biological and physical chemistry applications. They can be used for instance, as fluorescent labels to label almost any biological molecule, as well as to probe the physical and chemical environment of macromolecules. The nucleosides of this invention can also be derivitized as nucleotide triphosphates that can then be utilized as monomers for DNA synthesis. In one preferred embodiment, the pteridine nucleotides of Formula I are derivatized for DNA synthesis by protecting the reactive exocyclic amine, for example, $R^2$ can be a dimethylaminomethylenamino group, the 3'-hydroxyl can be derivatized as a phosphoramidite group and $R^7$ can be derivatized as a dimethoxytrityl group.

Moreover, the compounds of Formula I can be used as fluorescent labels. In certain embodiments, the pteridine nucleotides can be linked through the 5'-hydroxyl, the 3'-phosphate, or the 2'-hydroxyl (in the case of a ribofuranose) directly, or through a linker, to the composition it is desired to label. Such labeled compositions can include, but are not limited to, biological molecules such as antibodies, ligands, lipids, polysaccharides, cell surface receptors, and enzymes.

In addition, the pteridine nucleotide triphosphates of Formula I can be used in DNA amplification techniques such as, the polymerase chain reaction. For instance, a pair of PCR primers can be chosen that are complementary to the DNA sequences flanking a DNA sequence of interest. The PCR reaction mixture will contain one or more species of nucleotide triphosphates of Formula I. If the proper target sequences are present in the sample, the DNA sequence between the primers will be amplified. This amplified DNA sequence will then contain the fluorescent pteridine nucleotide triphosphates of the present invention.

Moreover, the compounds of this invention can be used as hybridization probes to detect the presence, absence, or quantity of a target nucleic acid. In one embodiment, this involves contacting the target nucleic acid with a nucleic acid probe where the nucleic acid probe comprises a compound of Formula I located in the probe. When the probe hybridizes to the target nucleic acid, the compound of Formula I is forced out of base stacking which relieves fluorescence quenching caused by base stacking. This results in multi-fold increases in fluorescence intensity. These as well as other applications and uses will be described in detail below.

III. Preferred Fluorescent Nucleosides and Their Synthesis

There is a great need for fluorescent nucleosides that are purine analogs, especially adenosine analogs, which are more stable and possess higher fluorescent quantum yields than the prior art compounds. The inventors have found that the compounds of Formula (I) are more stable and possess greater quantum yields than the compounds of the prior art.

As such, the present invention relates to compounds of Formula (I)

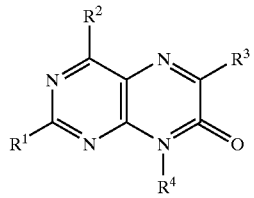

wherein $R^1$, $R^2$, $R^3$, $R^4$, $R^5$, $R^6$, $R^7$ and L have been defined above.

In Formula I, certain compounds are preferred. In one embodiment, compounds where $R^1$ is hydrogen, $R^2$ is amino or dimethylaminomethylenamino; $R^3$ is methyl; $R^4$ is L; $R^5$ is hydrogen; $R^6$ is hydrogen or β-cyanoethyl-N-diisopropyl phosphoramidite; and $R^7$ is hydrogen, dimethoxytrityl or a triphosphate are preferred.

Compounds of Formula I are more stable and have a higher fluorescence quantum yield than structurally similar compounds.

In another embodiment, compounds where $R^1$ is $C_1$–$C_6$ alkyl, especially methyl, $R^2$ is amino or dimethylaminomethylenamino; $R^3$ is methyl, $R^4$ is L; $R^5$ is hydrogen; $R^6$ is hydrogen or β-cyanoethyl-N-diisopropyl phosphoramidite, and $R^7$ is hydrogen, dimethoxytrityl or a triphosphate are preferred.

The synthesis of compounds of Formula I is accomplished by reacting a protected pteridine derivative with a chlorofuranose having its 3'- and 5'-hydroxyls protected as their 4-chlorobenzoyl or paratoluoyl esters to produce a pteridine nucleoside. Following coupling, the protecting groups can be removed and the 5'-hydroxyl converted to its dimethoxytrityl ether. Subsequent conversion of the 3'-hydroxyl to the H-phosphonate, phosphorarmidite, or hemisuccinate provides the compounds of Formula I.

More specifically, with reference to FIG. 2, 4,5,6-triaminopyrimidine (1), (see, J. Baddiley et al., *J. Chem. Soc.* 386 (1943)) and ethyl pyruvate are heated in glacial acetic acid for 2 hours. After cooling the precipitate is collected and washed with water and purified by recrystallization using a suitable solvent system, such as DMF/$H_2O$, to yield 4-amino-6-methyl-7(8H)-pteridone (3) (see, D. Söll et al., *Chem. Ber.* 96:2977 (1963)). Compounds wherein $R^1$ is an methyl group can be generated similarly by starting with 4,5,triamino-2-methylpyrimidine (2).

To covalently attach the furanose ring, compound (3) or (4) and DBU (1,8-diaza-bicyclo[5.4.0]-undec-7-ene) are stirred in an anhydrous solvent, such as acetonitrile, and then 2-deoxy-3,5-di-O-p-chlorobenzoyl-α-D-ribofuranosyl chloride (J. J. Fox et al., *J. Am. Chem. Soc.* 83.4066 (1961)) is added. Stirring is continued for 2 hours which generates compounds (5) and (6), respectively. Subsequent removal of the chlorobenzoyl protecting group using anhydrous methanol will yield compounds (7) or (8), respectively.

The 5'-hydroxyl of the nucleoside can then be blocked with a protecting group (preferably dimethoxytrityl). Means of coupling protecting groups are well known to those of skill in the art. This is accomplished by reaction of the nucleoside with dimethoxytrityl chloride in dry pyridine. Other protocols are generally known to those of skill in the art. More specifically, with reference to FIG. 2, compound (7) or (8) is reacted with 4,4'-dimethoxytrityl chloride in a suitable solvent, such as pyridine, to yield compound (9) or (10), respectively.

Where a protected amine is desired in the product, it can be introduced at any of several stages. For example, the starting pteridine can contain an amine substituent that is protected prior to further manipulation. Alternatively, an amine can be introduced at a later stage by conversion of an oxo moiety to a thione followed by amination with ammonia. Yet another method for introducing an amine uses a starting pteridine bearing a methylthio substituent in the 2-position. After coupling with the desired chlorofuranose, the protecting groups are removed and the methylthio group is displaced with ammonia.

The 3'-hydroxyl of the pteridine nucleoside can be converted to its respective hemisuccinate, phosphoramidite, H-phosphonate, or triphosphate using methods known to those of skill in the art. For example, conversion of the nucleoside 3'-hydroxyl to a hemisuccinate can be accomplished by reaction with succinic anhydride. Means of converting a nucleoside to a phosphoramidite are also well known to those of skill in the art.

Figure 2:
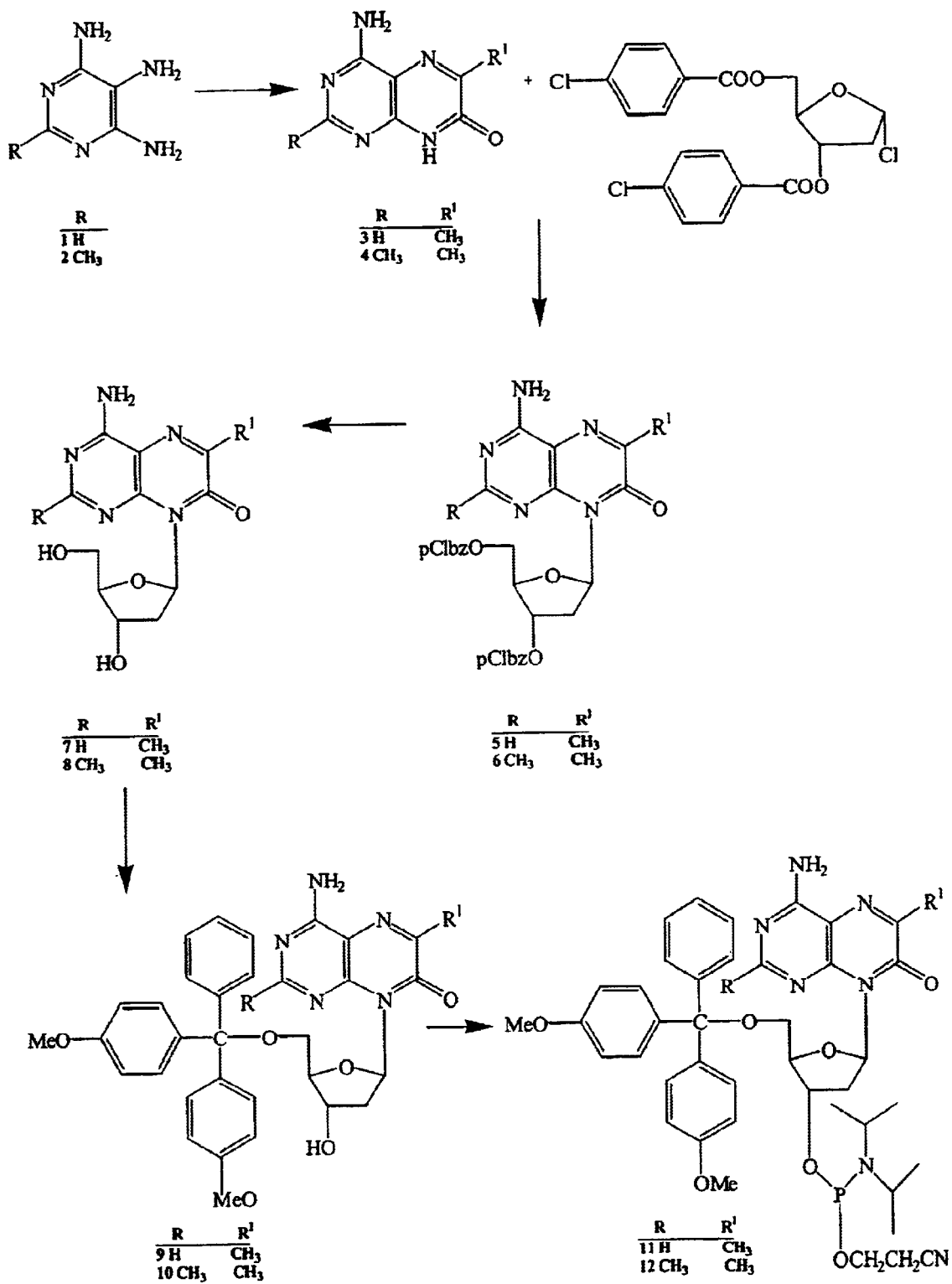
FIG. 2 illustrates a synthetic scheme of compounds of Formula I.
Figure 3:
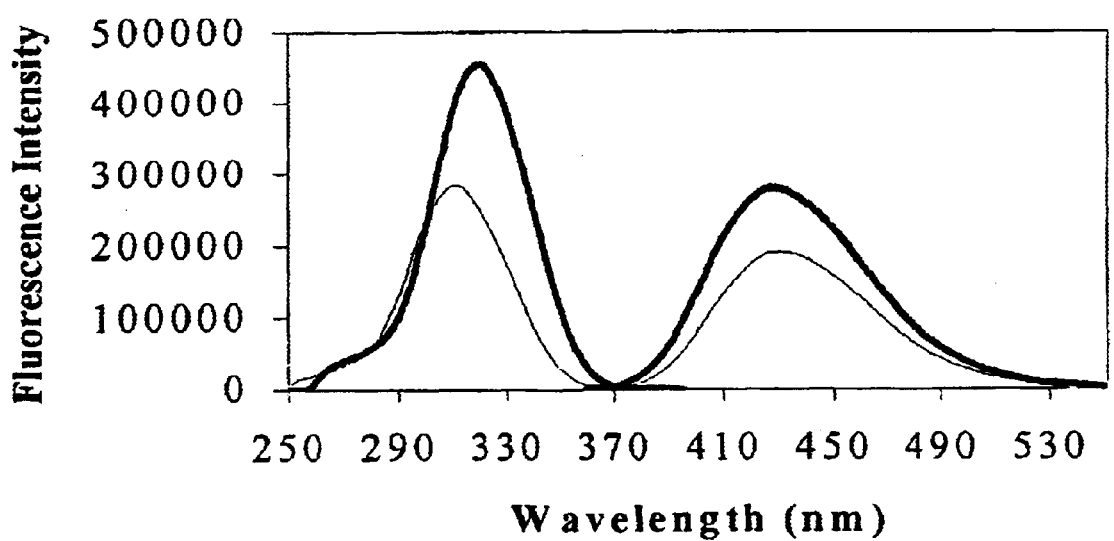
FIG. 3 illustrates excitation and emission scans of 6MAP (solid line—higher peaks) and DMAP (dashed line—lower peaks). Samples were measured in 10 mM Tris pH 7.5 at room temperature.

More specifically, with reference to FIG. 2, 4-amino-6-methyl-8-[-2-deoxy-5-O-(4,4'-dimethoxytrityl)-β-D-ribofuranosyl]-7(8H)-pteridone-3'-O-(2-β-cyanoethyl N-diisopropyl)phosphoramidite compound (11) or its methyl analog compound (12), can be synthesized starting from compound (9) or (10) respectively and bis-(N,N-diisopropylamino)-2-β-cyanoethoxyphosphane and 1H-tetrazole.

Similarly, means of converting a nucleoside to an H-phosphonate are also well known to those of skill in the art. In one approach, phosphorous (III) trichloride derivatives are used to directly phosphitylate the 3'-hydroxyl of the nucleoside. More specifically, phosphorous (III) triimidazolide can be used to phosphitylate the 3'-hydroxyl. This method is described in detail by Garegg et al., *Chemica Scripta* 25:280–282 (1985) and by Tocik et al., *Nucleic Acids Res.* 18:193 (1987). Similarly, the use of tris-(1,1,1,3,3,3-hexafluoro-2-propyl) phosphite to produce ribonucleoside-H-phosphonates is described by Sakatsume et al., *Nucleic Acids Res.* 17:3689–3697 (1989). The use of the same reagent to produce deoxynucleoside-H-phosphonates is described by Sakatsume et al., *Nucleic Acids Res.* 18:3327–3331 (1990). Other approaches to the derivatization of the 3'-hydroxyl to produce H-phosphonates may be found in Sekine et al., *J. Org. Chem.* 47:571–573 (1982), Marugg et al., *Tetrahedroni Lett.* 23:2661–2664 (1986), and Pon et al., *Tetrahedron Lett.* 26:2525–2528 (1985).

Derivatization of the 5'-hydroxyl as a triphosphate can be accomplished by a number of means known to those of skill in the art. Where the pteridine nucleoside has sufficient structural similarity to native nucleotides to act as an enzymatic substrate, the monophosphate may be synthesized chemically as described below and then enzymatically converted to the diphosphate and then to the triphosphate using the appropriate nucleotide monophosphate and diphosphate kinases respectively.

Alternatively, the nucleoside can be chemically derivatized as the triphosphate. This may be accomplished by reacting the nucleoside with trimethyl phosphate and POCl₃ and then adding a triethylammonium bicarbonate buffer to form the nucleotide monophosphate which can then be purified chromatographically. The nucleotide monophosphate is then activated using carbonyldiimidazole and coupled with tributylammonium pyrophosphate to form the nucleotide triphosphate. The nucleotide triphosphate can then be precipitated as a sodium salt.

IV. Oligonucleotide Synthesis

As previously discussed, the pteridine derivatives of the present invention are structurally analogous to adenosine. In certain aspects of the present invention, the compounds of Formula I are incorporated into an oligonucleotide, where they act as fluorescent tags. Because the compounds of Formula I are structurally analogous to the naturally occurring base, they do not alter the physical and chemical properties of the oligonucleotide as severely as currently available fluorescent tags. In some cases, the perturbations are so minimal as to allow the oligonucleotide to act as an enzyme substrate permitting the enzyme catalyzed reaction to occur even when the substitution has been made at a site known to be critical for the enzyme function. Thus the oligonucleotides of this invention are particularly useful in the investigation of DNA-protein interactions. In certain aspects, the compounds of Formula I can be at the terminal position of the oligonucleotide or, alternatively, an internal position. The oligonucleotide can contain one or more nucleotide monomers of Formula I. The nucleotide monomers can be the same or different. The compounds can be adjacent to one another or spatially separated. If the oligonucleotide contains more than one compound of Formula I their arrangement can be random or quite specific, e.g., being next only to purines or to pyrimidines etc.

As such, this invention relates to an oligonucleotide comprising one or more nucleotide monomers Formula I

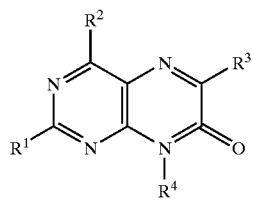

wherein $R^1$, $R^2$, $R^3$, $R^4$, $R^5$, $R^6$, $R^7$ and L have been defined above.

Compounds of Formula I wherein $R^6$ is β-cyanoethyl, N-diisopropyl phosphoramidite are preferred as oligonucleotide synthesis monomers. These compounds can generally be utilized in most commercial DNA synthesizers without modification of the synthesis protocol. However, where large scale synthesis is desired, or where it is desirable to incorporate sulfr groups or other modifications in the phosphate linkages, compounds of Formula I wherein $R^6$ is H-phosphonate are preferred as synthesis reagents. The synthesis and use of other phosphorous containing derivatives suitable for oligonucleotide synthesis is well known to those of skill in the art. These include, but are not limited to, a methyl phosphonate, a phosphorothioate, and a phosphotriester. Thus, in one preferred embodiment, the pteridine nucleotides of Formula I are derivatiz and protected for use as reagents in the synthesis of oligonucleotide. In particular, the reactive exocyclic amines are protected, for example $R^2$ is dimethylaminomethylenamino, the 3'-hydroxyl is derivatized as an H-phosphonate, or as a phosphoramidite and $R^7$ is dimethoxytrityl. Table 2 sets forth preferred oligonucleotides of the present invention.

The oligonucleotide of the present invention can be synthesized in solid phase or in solution. Generally, solid phase synthesis is preferred. Detailed descriptions of the procedures for solid phase synthesis of oligonucleotide by phosphite-triester, phosphotriester, and H-phosphonate chemistries are widely available. See, for example, Itakura, U.S. Pat. No. 4,401,796; Caruthers et al., U.S. Pat. Nos. 4,458,066 and 4,500,707, Beaucage et al., *Tetrahedron Lett.* 22:1859–1862 (1981); Matteucci et al., *J. Amer. Chem. Soc.* 103;3185–3191 (1981); Caruthers et al., *Genetic Engineering* 4:1–17 (1982); Jones, chapter 2, Atkinson et al., chapter 3, and Sproat et al., chapter 4, in Gait, ed. *Oligonucleotide Synthesis: A Practical Approach*, IRL Press, Washington D.C. (1984); Froehler et al., *Tetrahedron Lett.* 27:469–472 (1986); Froehler et al., *Nucleic Acids Res.* 14:5399–5407 (1986); Sinha et al., *Tetrahedron Lett.* 24:5843–5846(1983); and Sinha et al., *Nucl. Acids; Res.* 12:4539–4557 (1984).

Generally, the timing of delivery and concentration of reagents utilized in a coupling cycle will not differ from the protocols typical for unmodified commercial phosphoramidites used in commercial DNA synthesizers. In these cases, one can merely add the solution containing the pteridine derivatives of this invention to a receptacle on a port provided for an extra phosphoramidite on a commercial synthesizer (e.g., model 380B, Applied Biosystems, Foster City, Calif., USA). However, where the coupling efficiency of a particular derivatized pteridine compound is substantially lower than the other phosphoramidites, it may be necessary to alter the timing of delivery or the concentration of the reagent in order to optimize the synthesis. Means of optimizing oligonucleotide synthesis protocols to correct for low coupling efficiencies are well known to those of skill in the art. Generally, one merely increases the concentration of the reagent or the amount of the reagent delivered to achieve a higher coupling efficiency. Methods of determining coupling efficiency are also well known. For example, where the 5'-hydroxyl protecting group is a dimethoxytrityl (DMT), coupling efficiency may be determined by measuring the DMT cation concentration in the acid step (which removes the DMT group). DMT cation concentration is usually determined by spectrophotometrically monitoring the acid wash. The acid/DMT solution is a bright orange color. Alternatively, since capping prevents further extension of an oligonucleotide where coupling has failed, coupling efficiency may be estimated by comparing the ratio of truncated to full length oligonucleotide utilizing, for example, capillary electrophoresis or HPLC.

Solid phase oligonucleotide synthesis can be performed using a number of solid supports. A suitable support is one which provides a fiunctional group for the attachment of a protected monomer which will become the 3' terminal base in the synthesized oligonucleotide. The support must be inert to the reagents utilized in the particular synthesis chemistry. Suitable supports are well known to those of skill in the art. Solid support materials include, but are not limited, to polacryloylmorpholide, silica, controlled pore glass (CPG), polystyrene, polystyrene/latex, and carboxyl-modified Teflon. Preferred supports are amino-functionalized controlled pore glass and carboxyl-functionalized Teflon.

Solid phase oligonucleotide synthesis requires, as a starting point, a fully protected monomer (e.g., a protected nucleoside) coupled to the solid support. This coupling is typically through the 3'-hydroxyl (oxo when coupled) covalently bound to a linker which is, in turn, covalently bound to the solid support. The first synthesis cycle then couples a nucleotide monomer, via its 3'-phosphate, to the 5'-hydroxyl of the bound nucleoside through a condensation reaction that forms a 3'-5' phosphodiester linkage. Subsequent synthesis cycles add nucleotide monomers to the 5'-hydroxyl of the last bound nucleotide. In this manner an oligonucleotide is synthesized in a 3' to 5' direction producing a "growing" oligonucleotide with its 3' terminus attached to the solid support.

Numerous means of linking nucleoside monomers to a solid support are known to those of skill in the art, although monomers covalently linked through a succinate or hemisuccinate to controlled pore glass are generally preferred. Conventional protected nucleosides coupled through a hemisuccinate to controlled pore glass are commercially available from a number of sources (e.g., Glen Research, Sterling, Vermont, USA, Applied Biosystems, Foster City, Calif., USA, Pharmacia LKB, Piscataway, N.J., USA).

Placement of a pteridine nucleotide at the 3' end of an oligonucleotide requires initiating oligonucleotide synthesis with a fully blocked furanosyl pteridine linked to the solid support. In a preferred embodiment, linkage of the pteridine nucleoside is accomplished by first derivatizing the pteridine nucleotide as a hemisuccinate. The hemisuccinate can then be attached to amino-functionalized controlled pore glass in a condensation reaction using mesitylene-2-sulfonyl chloride/1-methyl-1H-imidazole as a condensing agent. Controlled pore glass functionalized with a number of different reactive groups is commercially available (e.g., Sigma Chemical, St. Louis, Mo., USA). A similar coupling scheme is described by Atkinson et al., chapter 3 in Gait, ed., *Oligonucleotide Synthesis: A Practical Approach*, IRL Press, Washington, D.C. (1984). Triisopropylbenzenesulfonyl chloride, imidazolides, triazolides or even the tetrazolides can also be used as condensing agents. Dicyclohexylcarbodiimide (DCC) and structural analogs are also suitable linkers. Other linkers and appropriate condensing groups are well known to those of skill in the art.

In a preferred embodiment, this invention relates to pteridine nucleotides in which the 3'-hydroxyl is derivatized as a hemisuccinate which may then be covalently bound to a solid support; more specifically to controlled pore glass. In this aspect, $R^2$ of Formula I is an amino group which is mono- or di-substituted with a protecting group, such as dimethylaminomethylenamino, or a p-nitrophenylethoxycarbonyl group, and $R^6$ is a hemisuccinate, or a hemisuccinate covalently bound to a solid support.

It is important to note that where the exocyclic amines are protected by the p-nitrophenylethoxycarbonyl group, the deprotection reagents may also cleave the ester function of the succinyl spacer linking the 3' terminal nucleoside to the solid support. In this case, the coupling scheme described by Stengele et al., *Tetrahedron Lett.* 18:2549–2552 (1990), is preferred. In this method, solid supports (dihydroxypropyl-CPG, 500 Å and 1400 Å, Fluka A G, Switzerland, Catalog Nos: 27754, 27764, 2770) are reacted first with N,N'-carbonyldiimiazole and then with 1,6-bismethylaminohexane as an aliphatic secondary amine spacer. This compound is then coupled with the appropriately protected 2'-nucleoside-3'-O-succinates and the free hydroxyl groups of the solid support are subsequently protected with acetic anhydride and 4-dimethylaminopyridine (DMAP). This linker is completely stable under the deprotection conditions used for p-nitrophenylethoxycarbonyl and p-nitrophenylethyl groups, while cleavage from the matrix can be achieved normally under hydrolytic conditions in concentrated ammonia in less than two hours.

Once the full length oligonucleotide is synthesized, the protecting groups are removed (the oligonucleotide is deprotected), and the oligonucleotide is then cleaved from the solid support prior to use. Where a non-cleavable linker is used, the oligonucleotide can be deprotected and left permanently attached to the support to produce an affinity column. Non-cleavable linkers are well known to those of skill in the art (See, e.g., WO/8501051, EP-A-9174879 and Duncan et al., *Anal. Biochem.*, 169, 104–108(1988)).

Cleavage and deprotection can occur simultaneously, or sequentially in any order. The two procedures can be interspersed so that some protecting groups are removed from the oligonucleotide before it is cleaved off the solid support and other groups are deprotected from the cleaved oligonucleotide in solution. The sequence of events depends on the particular blocking groups present, the particular linkage to a solid support, and the preferences of the individuals performing the synthesis. Where deprotection precedes cleavage, the protecting groups can be washed away from the oligonucleotide which remains bound on the solid support. Conversely, where deprotection follows cleavage, the removed protecting groups will remain in solution with the oligonucleotide. Often the oligonucleotide will require isolation from these protecting groups prior to use.

In a preferred embodiment, the protecting group on the 5'-hydroxyl is removed at the last stage of synthesis. The oligonucleotide is then cleaved off the solid support, and the remaining deprotection occurs in solution. Removal of the 5'-hydroxyl protecting group typically just requires treatment with the same reagent utilized throughout the synthesis to remove the terminal 5'-hydroxyl groups prior to coupling the next nucleotide monomer. Where the 5'-hydroxyl protecting group is a dimethoxytrityl group, deprotection can be accomplished by treatment with acetic acid, dichloroacetic acid or trichloroacetic acid.

Typically, both cleavage and deprotection of the exocyclic amines are effected by first exposing the oligonucleotide attached to a solid phase support (via a base-labile bond) to the cleavage reagent for about 1–2 hours. In this manner, the oligonucleotide is released from the solid support. The solution containing the released oligonucleotide is then heated for at least 20–60 minutes at about 80–90° C. so that the protecting groups attached to the exocyclic amines are removed. The deprotection step can, alternatively, take place at a lower temperature, but must be carried out for a longer period of time (e.g., the heating can be at 55° C. for 5 hours). In general, the preferred cleavage and deprotection reagent is concentrated ammonia.

Where the oligonucleotide is a ribonucleotide and the 2'-hydroxyl group is blocked with a tert-butyldimethylsilyl (TBDMS) moiety, the latter group may be removed using tetrabutylammonium fluoride in tetrahydrofuran at the end of synthesis. See, Wu et al., *J. Org. Chem.* 55:4717–4724 (1990). Phenoxyacetyl protecting groups can be removed with anhydrous ammonia in alcohol (under these conditions the TBDMS groups are stable and the oligonucleotide is not cleaved). The benzoyl protecting group of cytidine is also removed with anhydrous ammonia in alcohol.

Where the exocyclic amines are protected by the p-nitrophenyl-ethoxy-carbonyl group and the coupling to the solid support is via a 1,6-bis-methylaminohexane condensed with succinate nucleoside, the amino groups are preferably deprotected by treatment with a 1 M DBU (1,8-diaza-bicyclo[5.4.0]-undec-7-ene). Cleavage of the oligonucleotide from the solid support is then accomplished by treatment with concentrated ammonia.

The oligonucleotide of the present invention are not limited to short single stranded sequences. One of skill would recognize that while oligonucleotide synthesis typically has an upper limit of approximately 200 to 500 bases, a number of oligonucleotide can be ligated together to form longer sequences. In addition, oligonucleotide having complementary sequences can be hybridized together to form double-stranded molecules. Methods of hybridizing and ligating oligonucleotide to form longer double stranded molecules are well known (see, for example, Sambrook et al., *Molecular Cloning—A Laboratory Manual*, Cold Spring Harbor Laboratory, Cold Spring Harbor, N.Y., 1985).

In a preferred embodiment, the label oligonucleotide of this invention double as primers in an amplification reaction discussed in detail below. In this embodiment, one or more amplification primers are provided that each contain at least one compound of Formula I. In a particularly preferred embodiment, the compound of Formula I is one that will permit a polymerase to read through, but not add a corresponding nucleotide in the nucleic acid being extended by the polymerase. In still another embodiment, the label oligonucleotide doubles as an amplification primer and the loop that dequenches the compound of Formula I.

V. Use of Compounds of Formula I as Fluorescent Labels

One of skill will recognize that the pteridine derivatives of this invention can be used simply as fluorescent labels to label almost any biological molecule. The unprotected pteridines alone may be linked by the pteridine 1N or 8N, either directly or through a linker or spacer to a composition it is desired to label. Alternatively, the . pteridine nucleosides can be used as fluorescent labels. They can be linked preferably through the 5'-hydroxyl, the 3'-phosphate, or the 2'-hydroxyl (in the case of a ribofuranose) directly, or through a linker, to the composition it is desired to label. Such labeled compositions can include, but are not limited to, biological molecules such as antibodies, ligands, cell surface receptors, and enzymes.

The nucleic acid can be covalently coupled to the biological molecules either directly via an activated group (e.g., a hydroxyl, a carboxyl) or through a linker that provides reactive moieties that bind to the oligonucleotide and to the biological molecule respectively. Linkers suitable for attaching nucleic acids to biological molecules are well known. Generally, linkers are either hetero- or homo-bifunctional molecules that contain two or more reactive sites that may each form a covalent bond with the respective binding partner (the biological molecule or the nucleic acid). For example, compounds of Formula I can be joined by a peptide linker, by a straight or branched chain carbon chain linker, or by other linkers known by those of skill in the art. Heterobifunctional cross linking reagents such as active esters of N-ethylmaleimide have been widely used. See, for example, Lerner et al. *Proc. Nat. Acad. Sci.* (USA), 78:3403–3407 (1981) and Kitagawa et al. *J. Biochem.*, 79:233–236 (1976). Other linkers, such as those used in the synthesis of nucleic acids are also suitable (see, e.g., PCT Publication WO 85/01051, Pochet et al. *Tetrahedron.* 43: 3481–3490 (1987), Schwyzer et al., *Helv. Chim. Acta*, 67:1316–1327 (1984), Gait, ed. Oligonucleotide Synthesis: a Practical Approach, IRL Press, Washington D.C. (1984))

VI. Use of Compounds of Formula I in DNA Amplification

The compounds of Formula I can be derivitized as nucleotide triphosphates. The nucleotide triphosphate compounds of the present invention can be utilized as monomers for DNA synthesis in DNA amplification techniques such as polymerase chain reaction (see, Innis, et al., PCR Protocols. *A Guide to Methods and Application*, Academic Press, Inc., San Diego (1990)), ligase chain reaction (LCR) (see, Wu et al., *Genomics* 4:560 (1989), Landegren, et al., *Science* 241:1077 (1988) and Barringer, et al., *Gene* 89:117 (1990)), transcription amplification (see, Kwoh et al., *Proc. Natl. Acad. Sci. USA* 86:1173 (1989)) and self-sustained sequence replication (see, Guatelli, et al., *Proc. Natl. Acad. Sci.* USA, 87:1874 (1990)). Amplification utilizing the pteridine nucleotides of this invention provides a rapid assay for a particular DNA sequence. Where the presence or absence of a particular DNA sequence is diagnostic of a pathological condition (e.g., AIDS), amplification using the pteridine nucleotide triphosphates provides an extremely sensitive and rapid diagnostic tool.

For example, if PCR amplification is used, a pair of PCR primers will be chosen that are complementary to the DNA sequences flanking the DNA sequence of interest. The PCR reaction mixture will contain one or more species of nucleotide triphosphates of this invention. If the proper target sequences are present in the sample, the DNA sequence between the primers will be amplified. This amplified DNA sequence will contain the pteridine nucleotide triphosphates. The amplified sequence may be separated from the remaining monomers in the mixture by simple size fractionation (e.g., by using an NAP column, Pharmacia-LKB, Piscataway, N.J., USA) gel electrophoresis, or other techniques well known to those of skill in the art. The presence or absence of the amplified sequence can then be immediately detected by measuring the fluorescence of the sequence.

Alternatively, fluorescence polarization (FP) measurements can be used to detect a positive or negative PCR reaction without the necessity of separating the PCR products from the primers and nucleotide monomers. The technique uses pteridine nucleotide monomers or, alternatively, relatively short primers, about 25 base pairs each, that incorporate pteridine nucleotide monomers. After the PCR procedure is completed, the resulting mixture is analyzed using FP, by passing a beam of polarized light at an excitatory wavelength through the mixture. If the target sequence is not present in the starting mixture, the fluorescent primers will remain in solution as relatively small single-stranded fragments, or the fluorescent nucleotide monomers will remain in solution as relatively small molecules. Both the monomers and the short primer fragments will emit a relatively scattered and non-polarized fluorescent light. By contrast, if the target sequence is present, the pteridine monomers or the fluorescent primers will be incorporated into larger double-stranded segments which will move more slowly in response to the excitatory signal and the fluorescent light emitted by the mixture will be more polarized. See, EP No. 382433, which describes this technique in greater detail.

Certain nucleotide triphosphate compounds of Formula I are preferred. For instance, compounds of Formula I wherein $R^1$ is hydrogen or methyl, $R^2$ is $NH_2$, $R^3$ is methyl, $R^7$ is a triphosphate, $R^5$ is hydrogen, and $R^6$ is hydrogen are preferred.

VII. Use as Fluorescent Probes

In another embodiment, this invention provides methods of detecting the presence, absence, or quantity of a target nucleic acid by utilizing a nucleic acid that contains one or more compounds of Formula I. The fluorescence of a compound of Formula I is quenched when it is incorporated into an oligonucleotide (see, e.g., U.S. Pat. No. 5,525,711 and Hawkins et al. (1995) *Nucl. Acids Res.* 23:2872–2880). However, when the compound of Formula I is present as an insertion, fluorescence activity is partially or completely restored. Without being bound by a particular theory, it is believed that alteration of the normal conformation (e.g., base stacking) of the oligonucleotide at the location of the compound of Formula I reduces and/or eliminates the quench thereby causing an increase in fluorescence.

The methods involve contacting the target nucleic acid with a nucleic acid probe where the nucleic acid probe comprises a compound of Formula I located in the probe such that, when the probe hybridizes to the target nucleic acid, the compound of Formula I is present in a loop that does not participate in complementary base pairing with a nucleotide of the target nucleic acid. Next, detecting the fluorescence produced by the compound of Formula I when the probe forms a hybrid duplex with the target nucleic acid.

In certain embodiments, the nucleotide sequences of the oligonucleotide of this invention can be selected such that the normal base stacking of the compound of Formula I and/or its adjacent nucleotide is disrupted either through self-hybridization of the oligonucleotide or when the oligonucleotide hybridizes to a target nucleic acid or when the oligonucleotide participates in a protein/DNA interaction. This is typically accomplished when the compounds of Formula I are located in a loop(s).

The term nucleic acid loop, as used herein, refers to a region of one or more contiguous nucleic acids that do not participate in normal (e.g., purine/pyrimidine hydrogen bond formation) base pairing when the nucleic acid is hybridized to an otherwise complementary target nucleic acid. In a preferred embodiment, the loops of this invention are formed as insertions in nucleic acid sequences. The insertion can comprise one or more nucleotides. As used herein an insertion refers to the addition of one or more nucleotides into an oligonucleotide that is otherwise complementary to a target nucleic acid or target nucleotide subsequence. The insertion is thus recognized by reference to the target nucleic acid sequence or subsequence. One of skill will appreciate that an insertion need not be produced by actual physical insertion of one or more additional nucleotides (bases) into an already existing oligonucleotide, but reflects the presence of the extra nucleotide(s) with reference to a particular target sequence or subsequence. Thus, the insertion-containing oligonucleotide can be synthesized de novo. Alternatively, the insertion can be created by deleting one or more nucleotides in the target sequence or subsequence, or by synthesizing (e.g., polymerizing) a target sequence or subsequence lacking nucleotides corresponding to one or more nucleotides in the label oligonucleotide.

In one preferred embodiment, the loop ranges in length from about 1 to about 100 nucleotides when the probe hybridizes to the target nucleic acid. In particularly preferred probes, the loop is an insertion in the nucleic acid probe which is otherwise complementary to the target nucleic acid or to a contiguous subsequence of the target nucleic acid. In some preferred embodiments, the insertion is three nucleotides in length and comprises two nucleotides each adjacent to the compound of Formula I. In particularly preferred embodiments, at least one nucleotide adjacent to the compound of Formula I is a purine (e.g., adenosine), or is bordered by at least two adjacent purines (e.g., adenosine) in both the 5' and 3' direction. In another preferred embodiment, the insertion is a single base insertion, the compound of Formula I.

In yet another embodiment, the insertion is self-complementary and forms a hairpin in which the compound of Formula I is present in the loop of the hairpin and does not participate in complementary base pairing. The nucleotides comprising the loop can be selected such that they are not complementary to the corresponding nucleotides of the target nucleic acid when the probe is hybridized to the target nucleic acid and where the probe is complementary to at least two non-contiguous subsequences of the target nucleic acid.

The hairpin conformation can be one that is stabilized by hybridization to the target nucleic acid, or it can be a stable formation in the label oligonucleotide even when the label oligonucleotide is not hybridized to the target substrate. In this case, the base stacking of the label oligonucleotide is always disrupted resulting in a continually elevated fluorescence activity. The label oligonucleotide is an "always-on" label. The hairpin formation can be internal to the label oligonucleotide or alternatively can be formed at the terminus of the label oligonucleotide. The label oligonucleotide of this invention can include one or more of the above-described loops. In addition, any loop can include one or more compounds of Formula I. In another embodiment, the compound of Formula I is present in a terminal subsequence of the nucleic acid probe where the terminal subsequence does not hybridize to the target nucleic acid when the remainder of the nucleic acid probe hybridizes to the target nucleic acid. The terminal subsequence can form a terminal hairpin by hybridization with a second subsequence of the probe such that the compound of Formula I is present in a loop of the hairpin and does not participate in complementary base pairing.

One of skill in the art will appreciate that the methods and molecules of this invention can be used in a wide variety of contexts. Under conditions that permit self-hybridization, normal base stacking of compounds of Formula I is disrupted and the nucleotide fluoresces. These oligonucleotide continuously fluoresce and provide useful "always on" labels. Always on labels can also be produced by placing the compound of Formula I at the 3' or 5' terminus, most preferably at the 5' terminus. In this position, the compound of Formula I is not as quenched as when it is located within the oligonucleotide. The "always on" fluorescent labels can be used in a manner analogous to fluorescent labels (e.g., fluorescein, rhodamine, etc.) known in the prior art.

In a more preferred embodiment, the compounds of this invention are used to label molecules, more preferably biological molecules such as other nucleic acids, proteins, and the like. Particularly preferred molecules to be labeled include antibodies, growth factors, cell-surface receptors, lectins, hormones, and the like. Indeed, the molecules that can be so labeled include virtually any molecule that can be linked to a nucleic acid. The oligonucleotide of this invention can be linked to the subject molecules, e.g., proteins, or nucleic acids, directly, or through a linker.

Suitable linkers attaching nucleic acids to other molecules are well known to those of skill in the art. Generally linkers are either hetero or homobifunctional molecules that contain two or more reactive sites that can form a covalent bond with the nucleic acid and the molecule to which it is to be attached. For example, the label nucleic acids of this invention can be joined to the subject molecule by a peptide linker, by a straight or branched chain carbon chain linker, or by a heterocyclic carbon. The linkers can attach to convenient reactive moieties on the base (e.g., $NH_3$) to available hydroxyl groups on the ribose or to a terminal phosphate. Heterobifunctional cross linking reagents such as active esters of ethylmaleimide have been widely used (see, e.g., Lerner et al. (1981) *Proc. Nat. Acad. Sci. USA* 78:34033407 and Kitagawa et al. (1976) *J. Biochem.* 79:233236), and other suitable linkers are well known to those of skill in the art (see, e.g., Chapter 4 In Monoclonal Antibodies, Principles and Applications, Birch and Lennox, eds., Wiley-Liss, Inc., New York (1994)).

In another embodiment, the oligonucleotide of this invention have a nucleotide sequence that enables the molecules to act as molecular beacons. The term "molecular beacon," as used herein refers to a molecule capable of participating in a specific binding reaction and whose fluorescence activity changes when the molecule participates in that binding reaction. Preferred molecular beacons of this invention are label oligonucleotide that show little or no fluorescence activity when the molecule is free in solution and yet show a detectable increase in fluorescence activity when bound to their target substrate. The molecules are designed so that interaction (e.g., binding) with the substrate (target) molecule introduces a change in conformation of the label oligonucleotide that results in a reduction of the quenching of the compound of Formula I present in the label oligonucleotide. Such changes in conformation preferably involve a disruption of the normal base stacking of the compound of Formula I in the label oligonucleotide. Such disruptions are preferably produced by a one or more base pair mismatch between the label oligonucleotide and its target when the molecules are hybridized, by the formation of loops (e.g., hairpins) in the label oligonucleotide, by lack of complementarity between the compound of Formula I and the corresponding nucleotides in the target.

The compounds of Formula I possess fluorescence quantum yields higher than other structurally similar pteridine nucleotides.

Particularly preferred molecular beacons have a relative quantum yield in the unbound (quenched) state that ranges from undetectable to about 0.8, more preferably from undetectable to about 0.1 M and most preferably from undetectable to about 0.05.

Virtually any detectable change in fluorescence on binding is useful. However, the larger the change in fluorescence, the easier it is to detect the binding event. Thus, preferred molecular beacons show a 2-fold increase, more preferably at least a 5-fold increase and most preferably at least about 10 to about 20-fold increase in fluorescence intensity on binding to the target molecule.

The label oligonucleotide can also be used to detect interactions with nucleic acid binding proteins (or other molecules). The compounds of Formula I present in the label oligonucleotide are located so that the normal planar base stacking is disrupted when the label oligonucleotide is bound by a protein (e.g., rec A protein, PI nuclease, HIV integrase, estrogen receptor, etc.). Again, the disruption reduces or eliminates the "quench" resulting in an increase in fluorescence activity of the protein/label oligonucleotide complex. The increased fluorescence can be easily detected as discussed below. The label oligonucleotide sequence is selected to that the label oligonucleotide is recognized and bound by the particular protein (or other molecule) of interest.

In another preferred embodiment, the label oligonucleotides of this invention provide a means of detecting the presence and/or absence and/or quantifying the product of a nucleic acid amplification reaction. In this embodiment, the nucleotide sequence of the label oligonucleotide is selected so that the base stacking of the compound of Formula I is not disrupted unless an amplification product is present.

In one embodiment, the oligonucleotide does not participate in the amplification reaction. It is simply present as a separate indicator molecule. In this context, the label oligonucleotide nucleotide sequence is selected so that a loop containing the compound of Formula I is formed when the label oligonucleotide hybridizes to the amplification product. As amplification product is formed, the label oligonucleotide hybridizes to that product, disrupting the base pair stacking and thereby increasing its fluorescence activity. As long as the label oligonucleotide is present in a molar excess (of the amplification product) the change in fluorescence intensity in the reaction vessel is proportional to the amount of amplification product. However, it is also desirable to maximize the signal to noise ratio. Therefore, in a preferred embodiment, the molar excess of label oligonucleotide is kept as low as possible to minimize generation of a background signal.

In another embodiment, the compound of Formula I can be incorporated into one or more of the amplification primers such that when the primer is extended by formation of an amplification product, the extended primer forms a loop thereby dequenching the compound of Formula I.

In other embodiments, the fluorescent labels of this invention are particularly well suited for the detection of nucleic acid hybridization in a wide variety of contexts including, but not limited to, nucleic acid hybridization arrays, Southern blot hybridizations, in situ hybridization, and the like.

One of skill will appreciate that the fluorescent probes of the present invention can be immobilized on a substrate. The substrates include, but are not limited to, a glass substrate, (e.g., a high density array ), a solid support, or a gel. A high density array can be synthesized on a substrate by attaching photoremovable groups to the surface of a substrate, exposing selected regions of the substrate to light to activate those regions, attaching a nucleic acid monomer (e.g., a compound of Formula I) with a photoremovable group to the activated regions, and repeating the steps of activation and attachment until probes of the desired length and sequences are synthesized. The resulting array of probes can then be used to determine target nucleic acids. (See, e.g., Fodor et al. *Science*, 251:767–773 (1991) and U.S. Pat. No. 5,143,854.).

VIII. Hybridization with Label Oligonucleotides

The label oligonucleotide of this invention can be used as "always on" labels and simply attached to the molecule or article of interest just like any other fluorescent marker. Alternatively, the label oligonucleotides are used as molecular beacons whose fluorescence activity increases when the molecules hybridize to a target nucleic acid or nucleic acid subsequence or when the label oligonucleotides are bound by a target protein.

The nucleic acid hybridization simply involves providing a denatured label oligonucleotide probe and target nucleic acid under conditions where the probe and its target can form stable hybrid duplexes through complementary base pairing. As described above, the label oligonucleotide have nucleic acid sequences that introduce a change in conformation on hybridizing that increases the fluorescence activity of the compound of Formula I present in the label oligonucleotide. The resulting fluorescent hybrid duplexes are then detected, e.g., using a spectrofluorometer.

It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions can be selected to provide any degree of stringency. In a preferred embodiment, hybridization is performed at low stringency (e.g., about 20° C. to about 50° C., more preferably about 30° C. to about 40° C., and most preferably about 37° C. and 6×SSPE-T or lower for an oligonucleotide) to ensure hybridization and then subsequent washes are performed at higher stringency (e.g., typically, stringent conditions will be those in which the salt concentration is at most about 0.01 to 1.0 M Na ion concentration (or other salts) at pH 7.0 to 8.3 and the temperature is at least about 30° C. for short probes (e.g., 10 to 50 nucleotides) and at least about 50° C. or 60° C. for longer probes). Successive hybridizations can be performed at increasingly higher stringency (e.g., down to as low as 0.25×SSPE-T at 37° C. to 50° C.) until a desired level of hybridization specificity is obtained. Stringency can also be increased by addition of agents such as formamide.

Hybridization specificity can be evaluated by specific labeling of nucleic acids separated in gel electrophoresis and/or by evaluation of the signal to noise (background fluorescence), or by other methods well known to those of skill in the art. In general, there is a tradeoff between hybridization specificity (stringency) and signal intensity. Thus, in a preferred embodiment, the wash is performed at the highest stringency that produces consistent results and that provides a hybridization showing a readily detectable change in signal intensity (e.g., an increase in signal intensity of at least 20%, more preferably an increase in signal intensity of at least 50% and most preferably an increase in signal intensity of at least 100% (a doubling of signal intensity) over the background signal intensity.

Methods of selecting and optimizing nucleic acid sequences for hybridization to particular targets and/or internal hybridization and/or priming of particular templates are well known to those of skill in the art (see, e.g., Innis et al. (1990) PCR Protocols, A Guide to Methods and Applications, Innis et at., Academic Press, Inc., N.Y.). Such optimization is simplified by the use of nucleic acid sequence analysis software. Such software is well known to those of skill in the art and includes, but is not limited to, HyperPCR, Loop Viewer, MulFold, Primer, and Amplify (available on the internet at PubNet), GeneWorks7, GeneJocky, DNA Strider, LaserGene (DNAStar, Madison, Wis., USA), and the like.

IX. Signal Detection

Means of detecting the fluorescent signals produced by the label oligonucleotide of this invention are well known to those of skill in the art. Labeled target (sample) nucleic acids hybridized to the probes of the high density array are known to those of skill in the art. Typically detection is the same as that for any other fluorescent label. Such detection involves exposing the fluorescent moiety (i.e., the label oligonucleotide) to an excitation illumination at the absorption wavelength of the compound of Formula I. The light is absorbed and re-emitted at the emission wavelength of the compound of Formula I. Devices for detecting fluorescent labels are commercially available and include, but are not limited to, fluorometers, fluorescence microscopes, flow cytometers, fluorescence plate readers, and the like (see, e.g., Applied Imaging Corp., Santa Clara, Calif., USA; Perkin-Elmer Corp., Norwalk, Conn., USA; and Photon Technology International, South Brunswick, N.J., USA).

In a particularly preferred embodiment, fluorescence is detected using a PTI (Photon Technologies, Inc., New Brunswick, N.J., USA) spectrofluorometer with a double excitation monochromater, a water cooled photomultiplier, and a sample chamber coupled with a water bath (Pharmacia LKB, Piscataway, N.J., USA). Low volume measurements can be made using an "H" style cuvette with excitation over the long (e.g., 1 cm) path and emission through the short (e.g., 2 mm path). In another embodiment, 3 mm×3 mm square cuvettes with a brass adaptor have been successfully used.

In another embodiment the fluorescence of the label oligonucleotide can be detected indirectly through energy transfer through a second and even a third fluorophore. In this embodiment, a second fluorophore is provided that has an absorption wavelength at or about the emission wavelength of the compound of Formula I. When compound of Formula I is excited, the energy it releases is absorbed (e.g., through resonance energy transfer) by the second fluorophore which then fluoresces at its characteristic wavelength, This approach is particularly convenient where it is desired to shift the signal to a wavelength different than the characteristic fluorescence wavelength of the compound of Formula I. Resonance energy transfer systems are well known to those of skill in the art (see, e.g., Forster (1948) *Ann. Phys.* 2:55; Stryer et al. (1967) *Proc. Natl. Acad. Sci. USA* 58:719–726, and Stryler (1978) *Ann. Rev. Biochem.* 47:819).

X. Kits

An additional aspect of the invention relates to kits useful for the detection of nucleic acid/nucleic acid interactions and/or for the detection of protein/nucleic acid interactions and/or for the detection of amplification product. These kits take a variety of forms and can comprise one or more containers containing one or more label oligonucleotide of this invention. The label oligonucleotide can be "always on" probes or "molecular beacons" as described above. The label oligonucleotide can be simple "indicators" of a particular nucleic acid or protein target, or they can be amplification primers for amplification and detection of a particular target nucleic acid. Other optional components of the kit include, for example, a polymerase, a reaction vessel, a second fluorophore for detection through resonance energy transfer, the appropriate buffers for PCR or other amplification reactions, positive and negative controls for diagnostic application, and the like. In addition to the above components, the kit can also contain instructions for use.

In other aspects of this invention, the kits can be used for the synthesis of oligonucleotides. In this aspect, the kit comprises compounds of Formula I, preferably wherein $R^6$ is a phosphoramidite derivative.

In other aspects, the kits can be used to generate fluorescent labels. In this embodiment, the kit comprises a compound of Formula I and optionally contains a linked compound. Such linked compounds include, but are not limited to, biological molecules such as antibodies, lipids, liposomes, ligands, polysaccharides, cell surface receptors, and enzymes. These and other uses for kits will be readily apparent to those of skill in the art.

EXAMPLES

Example 1

This example illustrates the synthesis of the pteridone bases.

A. 4-Amino-6-methyl-7(8H)-pteridone (3). [D. Söll et al., *Chem. Ber.* 96:2977 (1963)].

4,5,6-Triaminopyrimidine (1) [J. Baddiley et al., *J. Chem. Soc.* 386 (1943)] (2.0 g, 16 mmoles) and ethyl pyruvate (2.2 mL, 19 mmoles) were heated in glacial acetic acid (20 mL) for 2 hours. Afer cooling the precipitate was collected, washed with water and purified by recrystallization from DMF/H$_2$O (350 mL, 1:1). Yield: 1.25 g (44%). M.p. >360° C. UV (pH 5), $\lambda_{max}$ (log ε): 218 (4.37), 243 (4.07), [291 (3.82)], 326 (4.02), [343 (3.89)]. $^1$H -NMR (D$_6$-DMSO): 2.34 (s, MeC(6)), 7.35+7.45 (2 bs, NH2); 8.12 (s, H—C(2)) 12.56 (bs, H—N(8)).

B. 4-Amino-2,6dimethyl-7(8H)-pteridone (4).

4,5,6-Triamino-2-methylpyrimidine (2) [B. Lythgoe et al., *J. Chem. Soc.* 315 (1944)] (0.5 g, 3.6 mmoles) and ethyl pyruvate (1 mL) were heated in AcOH (10 mL) and EtOH (10 mL) under reflux for 1 hour. After cooling the precipitate was collected and recrystallized from DMF/H$_2$O (90 mL, 1:1) with a little charcoal to give 0.372 g (54%) of colorless crystals. M.p. >300° C. (decomp.). V (pH 5), 245 (4.08). [291 (3.77)], [318 (4.00)], 331 (4.03), [345 (3.88)]. $^1$H-NMR (D$_6$-DMSO): 2.34 (s, 6H, Me-C(2), Me-C(6)), 7.32+7.42 (2 bs, NH$_2$), 12.43 (bs, H—N(8)). Anal. calcd. for C$_8$H$_9$N$_5$O (190.1): C 50.26, H 4.74, N 36.63; found: C 50.15, H 4.82, N 36.35.

Example 2

This example illustrates the coupling of a pteridone base to a deoxyribose.

A. 4-Amino-6-methyl-8(2-deoxy-3,5-di-O-p-chlorobenzoyl-β-D-ribofuranosyl)-7(8H)-pteridone (5). 4-Amino-6-methyl-7(8H)-pteridone (3) (1.54 g, 9 mmoles) and DBU (1.34 mL, 9 mmoles) were stirred in anhydrous acetonitrile (100 mL) for 30 min. Then 2-deoxy-3,5-di-O-p-chlorobenzoyl-α-D-ribofuranosyl chloride [J. J. Fox et al., *J. Am. Chem. Soc.* 83:4066 (1961)] was added and stirring continued for 2 hours. It was evaporated, the residue dissolved in dichloromethane (60 mL), washed with a saturated solution of NaCl (2×30 mL), the organic layer dried over Na$_2$SO$_4$, filtered and again evaporated. The crude product was dissolved in toluene (10 mL), put onto a silica gel column (5×11 cm) and eluted with toluene/EtOAc (2:1, 600 mL) and toluene/EtOAc (1:1, 400 mL). The main fraction was evaporated and then recrystallized from CHCl$_3$/MeOH to give 1.7 g (34%) colorless crystals. M.p. >187–189° C. UV (MeOH): 241 (4.66), 333 (3.96). $^1$H-NMR (D$_6$-DMSO): 2.38 (s, Me-C(6)), 2.55 (m, H$_\alpha$—C(2')), 3.18 (m, H$_\beta$(2')), 4.53 (m, 2 H—C(5')), 4.69 (m, H—C(4')), 5.94 (m, H—C (3')), 7.34 (m, H—C(1')), 7.5] (d, 2H p-Clbz), 7.59 (d, 2H p-Cl-bz), 7.79 (bs, NH$_2$), 7.93 (2d, 4H p-Clbz), 8.22 (s, H—C(2)).

Anal. calcd. for C$_{26}$H$_{21}$Cl$_2$N$_5$O$_6$ (570.4): C 54.75, H 3.71, N 12.28; found: C 54.52, H 3.80, N 12.28.

B. 4-Amino-2,6-dimethyl-8-(2deoxy-3,5di-O-p-chlorobenzoyl-β-D-ribofuranosyl) 7(8H)-pteridone (6).

4-Amino-2,6-dimethyl-7(8H)-pteridone (4) (1.58 g. 8.26 mmoles) was suspended in anhydrous acetonitrile (60 mL), DBU (1.23 mL, 8.26 mmoles) added and stirred for 15 min at room temperature. Then 2-deoxy-3,5-di-O-chlorobenzoyl-α-D-ribofuranosyl chloride (4.2 g, 10 mmoles) was added and the mixture stirred for 2 hours. The colorless precipitate was collected and recrystallized from CHCL$_3$/MeOH (1:2, 90 mL) to give 1.92 g (40%). M.p. >218–220° C. (decomp). UV (MeOH): 241 (4.66), 333 (3.96). $^1$H-NMR (D$_6$-DMSO): 2.36 (s, Me-C), 2.40 (s, MeC), 2.57 (m, H$_\alpha$—C(2')), 3.17 (m, H$_\beta$–C(2')), 4.53 (m, 2 H—C(5')), 4.69 (m, H—C(4')), 6.00 (m, H—C(3')), 7.30 (m, H—C(1')), 7.42 (bs, NH$_2$), 7.50 (d, 2H p-Clbz), 7.59 (d, 2h p-Clbz), 7.89 (d, m2H p-Clbz), 7.96 (d, 2H p-Clbz).

Anal. calcd. for C$_{27}$H$_{23}$Cl$_2$N$_5$O$_6$ (548.4): C 55.49, H 3.97, N 11.98; found: C 55.57, H 4.09, N 11.53.

C. 4-Amino-6-methyl-8-(2-deoxy-β-D-ribofuranosyl)-7(8H)-pteridone (7).

Compound (5) (0.5 g, 0.88 mmoles) was added to a solution of sodium (20 mg) in anhydrous MeOH (20 mL) and stirred at room temperature for 12 hours. It was then neutralized by AcOH and the suspension concentrated to 10 mL. The precipitate was collected, washed with MeOH and dried in high vacuum to give 0.16 g (62%). Cooling of the filtrate provided a second crop 0.05 g (19%). M.p. >190° C. decomposition. UV (MeOH): 248 (4.09), [292 (3.71)], 329 (3.93). $^1$H-NMR (D$_6$-DMSO): 2.01 (m, H$_\alpha$—C(2')), 2.36 (s, Me), 2.88 (m, H$_\beta$—C(2')), 3.54 (m, H—C(5')), 3.60 (m, H—C(5")), 3.67 (m, H—C(4')), 4.44 (m, H—C(3')), 4.72 (dd, HO—C(5')), 5.17 (d, HO—C(3')), 7.15 (m, H—C(1')), 7.52+7.70 (2s, NH$_2$), 8.20 (s, H—C(2)).

Anal. calcd. for C$_{12}$H$_{15}$N$_5$O$_4$ (293.3): C.49.13, H 5.16, N 23.88; found: C 49.34, H 5.18, N 23.78.

D. 4-Amino2,6-dimethyl-8-(2-deoxy-β-D-ribofuranosyl)-7(8H)-pteridone (8).

Compound (6) (0.78 g, 1.33 mmoles) was added to a solution of sodium (30 mg) in anhydrous MeOH (20 mL)

and stirred at room temperature for 12 hours. It was then neutralized by AcOH and the suspension concentrated to 10 mL. The precipitate was collected, washed with MeOH and dried in high vacuum to give 0.38 g (93%) of colorless crystals. M.p. >180° C. decomposition. UV (MeOH): 250 (4.03), [298 (3.74)], 333 (3.95) $^1$H-NMR (D$_6$-DMSO): 1.99 (m, H$_\alpha$—C(2')), 2.34 (s, Me), 2.37 (s, Me), 2.88 (m, H$_\beta$—C (2')), 3.53 (m, H—C(5')), 3.65 (m. H—C(5")), 3.74 (m, H—C(4')), 4.45 (m, H—C(3')), 4.66 (dd, HO—C(5')), 5.16 (d, HO—C(3')), 7.14 (m, H—C(1')), 7.38–7.57 (2s, NH$_2$) Anal. calcd. for C$_{13}$H$_{17}$N$_5$O$_4$ (307.3): C 50.81, H 5.58, N 22.79; found: C 50.34, H 5.80, N 23.08.

Example 3

This example illustrates the protection of O-5' of the deoxyribose.

A. 4-Amino-6-methyl-8[-2-deoxy-5-O-(4,4'-dimethoxytrityl)-β-D-ribofuranosyl ]-7(8H)-pteridone (9).

Compound (7) (1.25 g, 4.26 mmoles) was twice coevaporated with anhydrous pyridine (20 mL) and then dissolved in the same solvent (20 mL). Then 4,4'-dimethoxytrityl chloride (1.73 g, 5.1 mmoles) was added and stirred at room temperature for 12 hours. It was evaporated, the residue dissolved in CH$_2$Cl$_2$ (40 mL) and washed with saturated NaHCO$_3$ solution (2×20 mL). The organic phase was dried over Na$_2$SO$_4$, evaporated, the residue dissolved in toluene (5 mL) and put onto a silica gel column for chromatography with toluene/EtOAc (1:3, 400 mL) and toluene/EtOAc (1:1, 600 mL). The product fraction was evaporated and the resulting solid foam dried in high vacuum to give 2.16 g (85%). M.p. >90–105° C. UV (MeOH): [233 (4.52)], [278 (3.84)], 3.28 (3.94). $^1$H-NMR (D$_6$-MSO): 2.11 (m, H$_\alpha$—C (2')), 2.30 (s, Me-C(6')), 2.78 (m, H$_\beta$—C(2')), 3.15 (m, H—C(5')), 3.33 (m, H—C(5")), 3.69 (s, OMe), 3.70 (s, OMe), 3.94 (m, H—C(4')), 4.44 (m, H—C(3')), 5.17 (d, OH—C(3')), 6.77 (2d, 4H, trityl), 7.20 (m, 7H, trityl), 7.35 (m,2H, trityl), 7.50+7.67 (2 bs, NH$_2$), 8.11 (s, H—C(2).

Anal. calcd. for C$_{33}$H$_{33}$N$_5$O$_6$ (595.7): C 66.54, H 5.58, N 11.76; found: C 66.58, H 5.92, N 11.73.

B. 4-Amino-2,6-dimethyl-8-[-2deoxy-5-O-(4,4'-dimethoxytrityl)-β-D-ribofuranosyl ]-7(8H)-pteridone (10).

Compound (8) (0.57 g, 1.85 mmoles) was twice coevaporated with anhydrous pyridine (10 mL) and then dissolved in the same solvent (15 mL). Then 4,4'-dimethoxytrityl chloride (0.752 g, 2.22 mmoles) was added and stirred at room temperature for 12 hours. It was evaporated, the residue dissolved in CH$_2$Cl$_2$ (20 mL) and washed with saturated NaHCO$_3$ solution (2×20 mL). The organic phase was dried over Na$_2$SO$_4$, evaporated, the residue dissolved in toluene (5 mL) and put onto a silica gel column for chromatography with toluene/EtOAc (1:1, 300 mL) and toluene/EtOAc (1:3, 200 mL). The product fraction was evaporated and the resulting solid foam dried in high vacuum to give 0.785 g (70%). M.p. >105–120° C. UV (MeOH): [232 (4.46)], [258 (4.11)], 333 (3.96). $^1$H-NMR (D$_6$-DMSO): 2.08 (m, H$_\alpha$—C (2' )), 2.18 (s, Me-C(6)), 2.29 (s, MeC(6)), 2.76 (m, H$_\beta$—C (2')), 3.12 (m, H—C(5')), 3.39 (m, H—C(5")), 3.68 (s, OMe), 3.70 (s, OMe), 3.94 (m, H—C(4')), 4.45 (m, H—C (3')), 5.16 (d, OH—C(3')), 6.78 (2d, 4H, trityl), 7.17 (m, 7H, trityl), 7.33 (m, 2H, tityl), 7.34+7.67 (2 bs, NH$_2$). Anal. calcd. for C$_{33}$H$_{33}$N$_5$O$_6$×H$_2$O (627.7): C 65.06, H 5.94, N 11.16; found: C 64.92, H 5.92, N 11.23.

Example 4

This example illustrates the protection of O-3 of the deoxyribose.

A. 4-Amino-6-methyl-8-[-2deoxy-5-O-(4,4'-dimethoxytrityl)-β-D-ribofuranosyl]-7(8H)-pteridone-3'-O-(H-β-cyanoethyl N-diisopropyl)phosphoramidite (11).

Compound (9) (1.25 g, 2.1 mmoles), bis-(N, Ndiisopropylamino)-H-β-cyanoethoxyphosphane (0.95 g, 3.1 mmoles) and 1H -tetrazole (74 mg., 1.05 mmoles) were dissolved in anhydrous CH$_2$Cl$_2$ (30 mL) and stirred at room temperature under nitrogen atmosphere for 12 hours. It was diluted with CH$_2$Cl$_2$ (10 mL), washed with a saturated NaHCO$_3$ solution (2×10 mL), the organic phase dried over Na$_2$SO$_4$ and then evaporated. The solid foam was dissolved in toluene (3 mL), put onto a silica gel column (12×5 cm) for chromatography with toluene/EtOAc (1:1, 500 mL, containing a few drops of triethylamine). The product fraction was again evaporated to give 1.46 g (86%) of a solid colorless foam. M.p. >70–75° C. UV (MeOH): [233 (4.49)], [278 (3.81)], 328 (3.91). $^1$H-NMR (D$_6$-DMSO): 0.92–1.07 (m, 2 CHMe$_2$), 2.29 (s, Me-C(6)), 2.30 (m, H$_{\alpha-C}$(2')), 2.59 (t, OCH$_2$CH$_2$CN), 2.85 (m, H$_\beta$—C(2')), 3.12 (m, H—C(5')), 3.27 (m, H—C(5")), 3.38–3.57 (m, 2 CHMe$_2$, OCH$_2$CH$_2$CN)), 3.68 (s, 2 OMe), 4.06 (m, H—C(4')), 4.71 (m, H—C(3')), 6.76 (m, 4H, trityl), 7.19 (m, 7H, trityl, H—C(1')), 7.33 (m, 2H, trityl), 7.51+7.68 (2 bs, NH$_2$), 8.09 (s, H—C(2)).

Anal. calcd. for C$_{42}$H$_{50}$N$_7$O$_7$P (795.9): C 63.38, H 6.33, N 12.32; found: C 63.62, H 6.39, N 11.84.

B. 4-Amino-2,6-dimethyl-8-[-2-deoxy-5-O-(4,4'-dimethoxytrityl)-β-D-ribofuranosyl]-7(8H)-pteridone-3'-O-(H-β-cyanoethyl N-diisopropyl)phosphoramidite (12).

Compound (10) (0.61 g, 1 mmol), bis-(N, Ndiisopropylamino)-H-β-cyanoethoxyphosphane (0.45 g 1.5 mmoles) and $^1$H -tetrazole (35 mg, 0.5 mmoles) were dissolved in anhydrous CH$_2$Cl$_2$ (15 mL) and stirred at room temperature under nitrogen atmosphere of 12 hours. It was diluted with CH$_2$Cl$_2$ (10 mL), washed with a saturated NaHCO$_3$ solution (2×10 mL), the organic phase dried over Na$_2$SO$_4$ and then evaporated. The solid foam was dissolved in toluene (5 mL), put onto a silica gel column (12×1.5 cm) for chromatography with toluene/EtOAc (3:2, 150 mL, containing a few drops of triethylamine). The product fraction was again evaporated to give 0.69 g (85%) of a solid colorless foam. UV (MeOH): [231 (4.48)], [258 (4.13)], 334 (3.95). $^1$H-NMR (D$_6$-DMSO): 0.88–1.01 (m, 2 CHMe$_2$), 2.29 (s, Me-C(2)), 2.30 (s, Me-C(6)), 2.30 (m, H$_{\alpha-C}$(2')), 2.59 (t, OCH$_2$CH$_2$CN), 2.83 (m, H$_\beta$—C(2')), 3.11 (m, H—C (5')), 3.25 (m, H—C(5")), 3.38–357 (m, 2 CHMe$_2$, OCH$_2$CH$_2$CN), 3.69 (s, 2 OMe), 4.10 (m, H—C(4')), 4.73 (m, H—C(3')), 6.75 (m, 4H, trityl), 7.19 (m, 7H, trityl), H—C(1')), 7.33 (m, 2H, trityl), 7.33+7.54 (2 bs, NH$_2$).

Anal. calcd. for C$_{43}$H$_{52}$N$_7$O$_7$P (809.9): C 63.77, H 6.47, N 12.11; found: C 63.70, H 6.50, N 12.01.

Example 5

This example sets forth the synthesis of oligonucleotides using compounds of Formula I.

Oligonucleotide Synthesis and Purification

Probes were synthesized as phosphoramidites and incorporated directly into oligonucleotides using an Applied Biosystems Model 392 (Foster City, Calif.) automated DNA synthesizer following standard protocols recommended by the manufacturer. The fluorophore phosphoramidite was placed in bottle position 5 on the synthesizer and treated in the same way as the standard phosphoramidites. Table 2 lists sequences of oligonucleotides made using monomers of the present invention. The probe-containing synthetic oligonucleotides were treated in the same way as standard oligonucleotides throughout synthesis and de-blocking procedures. Purification of all strands was done by 20% denaturing polyacrylamide gel electrophoresis (19:1 acrylamide:bis). Bands were detected by UV shadowing, excised, and extracted using an Elutrap (Schleicher and Schuell, Concord, N.H.) electrical elution device. Double strands were formed by combining complementary strands at equimolar concentrations, heating to >85° C. and allowing to cool to room temperature. Comparison of fluorescence intensity between single and double stranded oligonucleotides was done after adding an excess of non-fluorophore containing strand to insure that all of the fluorophore containing strands were annealed.

Melting Temperatures

Melting temperatures of double-stranded oligonucleotides were measured by monitoring absorbance hyperchromicity at 260 nm in an HP spectrophotometer equipped with a Hewlett-Packard 89090A Peltier temperature controller. Samples were measured in 10 mM Tris, pH 7.5, with a NaCl concentration of 10 mM. Temperature was increased by 1° C. per minute with a 1 min equilibration time between measurements.

P1 Nuclease Digestion

P1 Nuclease was from Penicillium citrinum (Boehringer Mannheim Biochemica). Oligonucleotides were digested with P1 nuclease using 3 Units in a total volume of 100 $\mu$l. A fluorescence scan of starting material was compared with the fluorescence scan of the products after incubation at 37° for 19 hours. The ratio of these two scans was compared to the ratio of the relative quantum yield of the oligonucleotide used in the starting material and the relative quantum yield of the monomer form of the fluorophore being examined.

Spectroscopic Analysis

Fluorescence measurements were done on a PTI (Photon Technologies, Inc., New Brunswick, N.J.) spectrofluorometer equipped with a 75 Watt xenon arc lamp using a double excitation monochromater and a water cooled photomultiplier. The system was interfaced with a Pharmacia Multitemp LKB water bath temperature controller (Pharmacia). Small volume samples were measured in 3 mm×3 mm quartz cuvettes using custom built brass adaptors. Relative quantum yield measurements were done on samples measuring <0.12 at the excitation wavelength in 10 mM Tris, pH 7.5, at room temperature.

Excitation was at 350 nm and the emission wavelength was 450 nm. Corrected emission spectra were integrated and referenced to quinine sulfate (quantum yield 0.51). A Hewlett-Packard Model 8452a spectrophotometer (Palo Alto, Calif.) was used for UV-VIS analysis. Lifetime measurements were obtained by fitting a multi-exponential model to time-correlated single photon counting decay data, using a weighted nonlinear least-square method (see, Grinvald et al., *Anal. Biochem.*, 59, 583–598, (1974)). Goodness of fit was assessed with the $\chi^2$ function. (see, Badea et al., *Methods in Enzymology*, 61, 378–425, (1979)). For decay-associated spectra (DAS), time resolved data were obtained on samples by excitation at 330 nm and were observed every 10 nm over the emission band. The excitation pulse ("lamp") profile was obtained with a light-scattering suspension (Ludox) from Sigma. Further instrumentation details were as previously described. (see, Chen et al. *Biochemistry*, 30, 5184–5195, (1991); Knutson, et al. *Biochemistry*, 21, 4671–4679, (1982)). Deconvolution was routinely included in data analysis for the excitation pulse, which had an instrumental half-width of 800 ps (see, Chen et al. *Biochemistry*, 30, 5184–5195, (1991)). A convolved multi-exponential model, I'(t), describing the time course of fluorescence intensities (Eq. I) was fit to the fluorescence decay data $$I'(t) = \int L(t')I(t'-t)dt' \qquad \text{Equation 1}$$

Where L(t) is the lamp function (response of the instrument to the test laser pulse and $$I(t) = \sum_{i=1}^{n} \alpha_i e^{(-t/\tau_i)} \qquad \text{Equation 2}$$

Where I(t) is the fluorescence intensity, $\alpha_i$ are the pre-exponentials, and $\tau_i$ are the lifetimes. Total fluorescence intensity, $$I = \sum_{i=1}^{n} \alpha_i \tau_i,$$

and the percentage intensity from each component of the multi-exponential model is $\%I_i = \alpha_i \tau_i / I \times 100$. Mean lifetimes (intensity weighted lifetime, $\tau_m$) and the species-concentration-weighted lifetime <τ> are defined as:

$$\tau_m = \frac{\sum_{i=1}^{n} \alpha_i \tau_i^2}{\sum_{i=1}^{n} \alpha_i \tau_i} \qquad \text{Equation 3}$$

And $$\langle \tau \rangle = \frac{\sum_{i=1}^{n} \alpha_i \tau_i}{\sum_{i=1}^{n} \alpha_i \tau_i} \qquad \text{Equation 4}$$

Assessment of the degree of departure from mono-exponential decay was determined by comparing relative magnitudes of the pre-exponentials ($\alpha_i$), the percentage contribution to the intensity ($I_s$) of each component, and the difference between $\tau_m$ and <τ>. When a decay is made up of components differing greatly in lifetime, $\tau_m$ Will be much longer than <T>.

For complex systems, DAS are the emission spectra that belong to each lifetime obtained from fluorescence decay surfaces (see, Knutson et al., *Biochemistry*, 21, 4671–4679, (1982)). DAS were used to dissect the heterogeneity of the emission but they do not, in themselves, specify its origin. Lifetimes were obtained by global analysis of the entire surface. Viewing DAS as plots of the pre-exponential constants ($a_i$) at each wavelength, these spectra can be normalized to provide the intensity contribution from each component. We evaluated the relationship between quantum yield and lifetimes, to better understand the mechanisms of quenching involved when pteridines are inserted into an oligonucleotide. For quenching events occurring during the excited state (pure dynamic quenching) where quenching competes with fluorescence, $$Q = \frac{\tau}{\tau_n} \quad \text{Equation 5}$$

Where Q is the quantum yield, τ is the measured lifetime, and $\tau_n$ is the natural, or radiate, lifetime (i.e., one that would be observed for Q=1). Deviations from Equation 5 such that $\tau/Q > \tau_n$ signify static (or quasi-static) quenching (see, Werner et al. *Photochem. Photobiol.*, 29, 905–914, (1979)), which in turn is usually due to ground-state formation of non-fluorescent complexes. Therefore, Equation 5 is an indicator of whether a quenching mechanism operates predominantly in the excited or ground state. For application to a heterogeneous solution, Eq. 5 may be modified to use a mean lifetime that is the sum of the contributions from each component, namely <τ>(see, Werner et al., *Photochem. Photobiol.*, 29,905–914, (1979)).

RESULTS

TABLE 1

Fluorescence of DMAP and 6MAP monomers

|  | $Ex_{(max)}$ | $Em_{(max)}$ | $Q_{rel}$ | τ(ns) |
|---|---|---|---|---|
| 6MAP compound 11 | 320 | 430 | 0.39 | 3.8 |
| DMAP compound 12 | 310 | 430 | 0.48 | 4.8 |

Table 1: Fluorescence properties of the two adenosine analogues, 6MAP (compound 11) and DMAP (compound 12). Samples were measured in 10 mM Tris pH 7.5 at room temperature. Abbreviations: $Ex_{max}$, excitation maximum; $Em_{max}$ emission maximum; $Q_{rel}$, relative quantum yield; τ, lifetime in nanoseconds.

Relative quantum yields, excitation and emission maxima and lifetimes of the monomer form of 6MAP (compound 11) and DMAP (compound 12) are presented in Table 1. Each probe was found to be stable in ambient light and at room temperature for >24 hours. Both of these compounds exhibited mono-exponential decay patterns in the decay associated spectra.

TABLE 1

Relative quantum yields of oligonucleotides containing 6MAP or DMAP

| SEQ ID NO: | Sequence (5' → 3') | | $Q_{rel}$ |
|---|---|---|---|
| | | w/6MAP | |
| 1 | gtg tgg Faa atc tct agc agt | PTR21 | 0.010 |
| 2 | gtg tgg aaa Ftc tct agc agt | PTR22 | 0.020 |
| 3 | gtg tgg aaa atc tct Fgc agt | PTR23 | 0.018 |
| 4 | act gct Fga gat ttt cca cac | PTR24 | |
| 5 | act gct agF gat ttt cca cac | PTR25 | 0.011 |
| 6 | act gct agc cFt ttt cca cac | PTR28 | 0.041 |
| 7 | att cca caa Fgc cgt gtc a | HP21 | 0.010 |
| 8 | aga ggt gtc cFc ctg tgg aga | HP22 | <0.01 |
| 9 | aga ggt gta cFa gtg tgg aga | HP23 | 0.012 |
| 10 | aga ggt gta aFa atg tgg aga | HP24 | <0.01 |
| | | w/DMAP | |
| 11 | gtg tgg Faa atc tct agc agt | PTR31 | 0.023 |
| 12 | gtg tgg aaa Ftc tct agc agt | PTR32 | 0.022 |
| 13 | gtg tgg aaa atc tct Fgc agt | PTR33 | 0.01 |
| 14 | act gct Fga gat ttt cca cac | PTR34 | 0.012 |
| 15 | act gct agF gat ttt cca cac | PTR35 | 0.017 |
| 16 | act gct aga gFt ttt cca cac | PTR36 | 0.019 |
| 17 | act gct aga gat ttt ccF cac | PTR37 | 0.11 |
| 18 | act gct agc cFt ttt cca cac | PTR38 | 0.11 |
| 19 | att cca caa Fgc cgt gtc a | HP31 | 0.02 |
| 20 | aga ggt gtc cFc ctg tgg aga | HP32 | <0.01 |
| 21 | aga ggt gta cFa gtg tgg aga | HP33 | 0.02 |
| 22 | aga ggt gta aFa atg tgg aga | HP34 | <0.01 |

Table 2: Relative quantum yields of oligo's listed in Table 2 were measured at room temperature in 10 mM Tris pH 7.5. The optical density of each was determined (at the excitation wavelength, 350 nm) and then each was scanned from 360 to 550 nm. The integral of the area under the emission curve was then used to calculate the relative quantum yield using quinine sulfate (Q=0.51) as the standard.

Table 2: exhibits the relative quantum yields of a series of oligonucleotides containing either of the two probes. In each row, F denotes the position of the probe within the sequence. Oligonucleotides containing 6MAP are numbered from 21 to 28 and those containing DMAP are numbered from 31 to 38. The sequences of the two series are identical. For example, PTR21 and PTR31 are identical in sequence, differing only in the identity of the probe (6MAP for PTR21 and DMAP for PTR31).

TABLE 3

Melting temperatures of Oligonucleotides containing 6MAP or DMAP

| Oligo w/6MAP | $T_m$ | Oligo w/DMAP | $T_m$ |
|---|---|---|---|
| PTR21 | 56.1° | PTR31 | 52.4° |
| PTR22 | 53.5° | PTR32 | 51.8° |
| PTR23 | 54.8° | PTR33 | 53.8° |
| PTR24 | 57.2° | PTR34 | 54.6° |
| PTR25 | 55.3° | PTR35 | 57.0° |
| | | PTR36 | 51.6° |
| | | PTR37 | 51.0° |
| | | Control | 57.8° |

Table 3: Melting temperatures in degrees Centigrade. Samples were prepared from purified oligonucleotides diluted in 10 mM Tris pH 7.5 with 10 mM NaCl. Equimolar amounts of each strand were combined and heated to 85° C. for 2 minutes and allowed to cool to room temperature. Melting temperatures of double-stranded oligonucleotides were measured by monitoring absorbance hyperchromicity at 260 nm. Melting temperatures of oligonucleotides containing either 6MAP or DMAP are shown in Table 3.

Each probe was tested for its ability to pair with bases other than thymidine. Tm's of the pairing with other bases are listed in Table 4.

TABLE 4

Tm's of the Pairing with other Bases

| | Paired w/T | Paired w/A | Paired w/C | Paired w/G |
|---|---|---|---|---|
| PTR22 (6MAP) | 53.5° | 43.8° | 42.8° | 45.2° |
| PTR32 (DMAP) | 51.8° | 45.2° | 45.6° | 46.8° |

Table 4: Melting temperatures in degrees Centigrade for oligonucleotides containing 6MAP or DMAP paired with complementary strands with substitutions of T, A, C, or G as pairing partner for the probe. See Table 2 for sequences.

TABLE 5

Fluorescence of 6MAP or DMAP containing oligonucleotides

| | $Q_{rel}$ | $\tau_1$ (ns) | $\alpha_1$ | %I | $\tau_m$ (ns) | $<\tau>$(ns) |
|---|---|---|---|---|---|---|
| 6MAP | | | | | | |
| PTR21 | 0.01 | $\tau_1 = 0.69$ | $\alpha_1 = 0.30$ | 30 | 2.58 | 2.15 |
| | | $\tau_2 = 2.78$ | $\alpha_2 = 0.70$ | 70 | | |
| PTR25 | 0.02 | $\tau_1 = 2.93$ | | | | |
| PTR27 | | $\tau_1 = 0.29$ | $\alpha_1 = 0.40$ | 40 | 2.26 | 1.26 |
| | | $\tau_2 = 1.54$ | $\alpha_2 = 0.5$ | 53 | | |
| | | $\tau_3 = 4.73$ | $\alpha_3 = 0.07$ | 7 | | |
| PTR28 | 0.041 | $\tau_1 = 0.17$ | $\alpha_1 = 0.38$ | 38 | 1.82 | 1.09 |
| | | $\tau_2 = 1.15$ | $\alpha_2 = 0.40$ | 40 | | |
| | | $\tau_3 = 2.56$ | $\alpha_3 = 0.22$ | 22 | | |
| HP21 | 0.01 | $\tau_1 = 0.69$ | $\alpha_1 = 0.41$ | 41 | 2.85 | 2.16 |
| | | $\tau_2 = 3.18$ | $\alpha_2 = 0.59$ | 59 | | |
| HP22 | >0.01 | $\tau_1 = 0.61$ | $\alpha_1 = 0.52$ | 52 | 2.68 | 1.81 |
| | | $\tau_2 = 3.12$ | $\alpha_2 = 0.48$ | 48 | | |
| HP23 | 0.012 | $\tau_1 = 0.48$ | $\alpha_1 = 0.59$ | 59 | 2.13 | 1.34 |
| | | $\tau_2 = 2.58$ | $\alpha_2 = 0.41$ | 41 | | |
| DMAP | | | | | | |
| PTR32 | 0.02 | $\tau_1 = 0.40$ | $\alpha_1 = 0.39$ | 39 | 2.7 | 1.92 |
| | | $\tau_2 = 2.90$ | $\alpha_2 = 0.61$ | 61 | | |
| PTR38 | 0.11 | $\tau_1 = 0.77$ | $\alpha_1 = 0.42$ | 42 | 2.46 | 1.95 |
| | | $\tau_2 = 2.80$ | $\alpha_2 = 0.58$ | 58 | | |
| HP33 | 0.02 | $\tau_1 = 0.28$ | $\alpha_1 = 0.65$ | 65 | 2.14 | 1.06 |
| | | $\tau_2 = 2.52$ | $\alpha_2 = 0.35$ | 35 | | |

Table 5: Measurements were taken in 10 mM Tris buffer, pH 7.5 at room temperature. Abbreviations: $Ex_{max}$, excitation maximum; $Em_{max}$, emission maximum; $Q_{rel}$, relative quantum yield; $\tau_x$, lifetime for each component of a multi-exponential model; $\alpha_i$, pre-exponential for each component of a multi-exponential model; %I, percentage fluorescence intensity for each component of a multi-exponential model; $<\tau>$, species-concentration-weighted lifetime; $\tau_m$, intensity-weighted lifetime in nanoseconds.

P1 Nuclease Digestion of 6MAP or DMAP Containing Single Strands

To determine that quenching within oligonucleotides is a function of incorporation into a strand, and not from degradation of the probe during DNA synthesis, a P1 nuclease digestion was performed on separate strands containing either 6MAP or DMAP. In each case the resulting increase in fluorescence intensity compared to the fluorescence intensity of the undigested equivalent formed a ratio that was equivalent to the ratio of the quantum yield for the single stranded oligonucleotide and the quantum yield for the monomer form.

Figure 4:
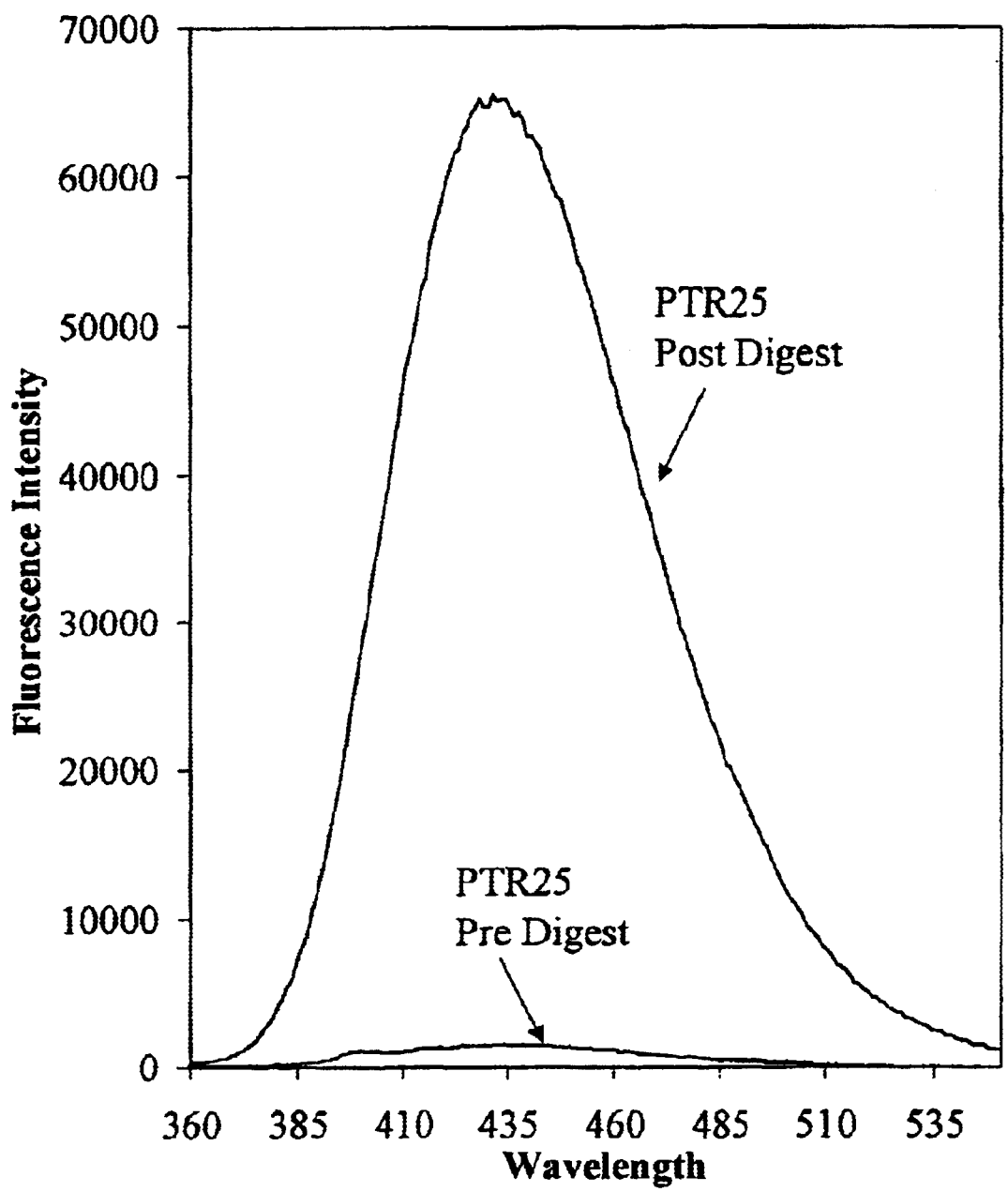
FIG. 4 illustrates effects of P1 nuclease digestion on oligonucleotides containing 6MAP. Reaction mixtures were incubated overnight at 37° C.
Figure 5:
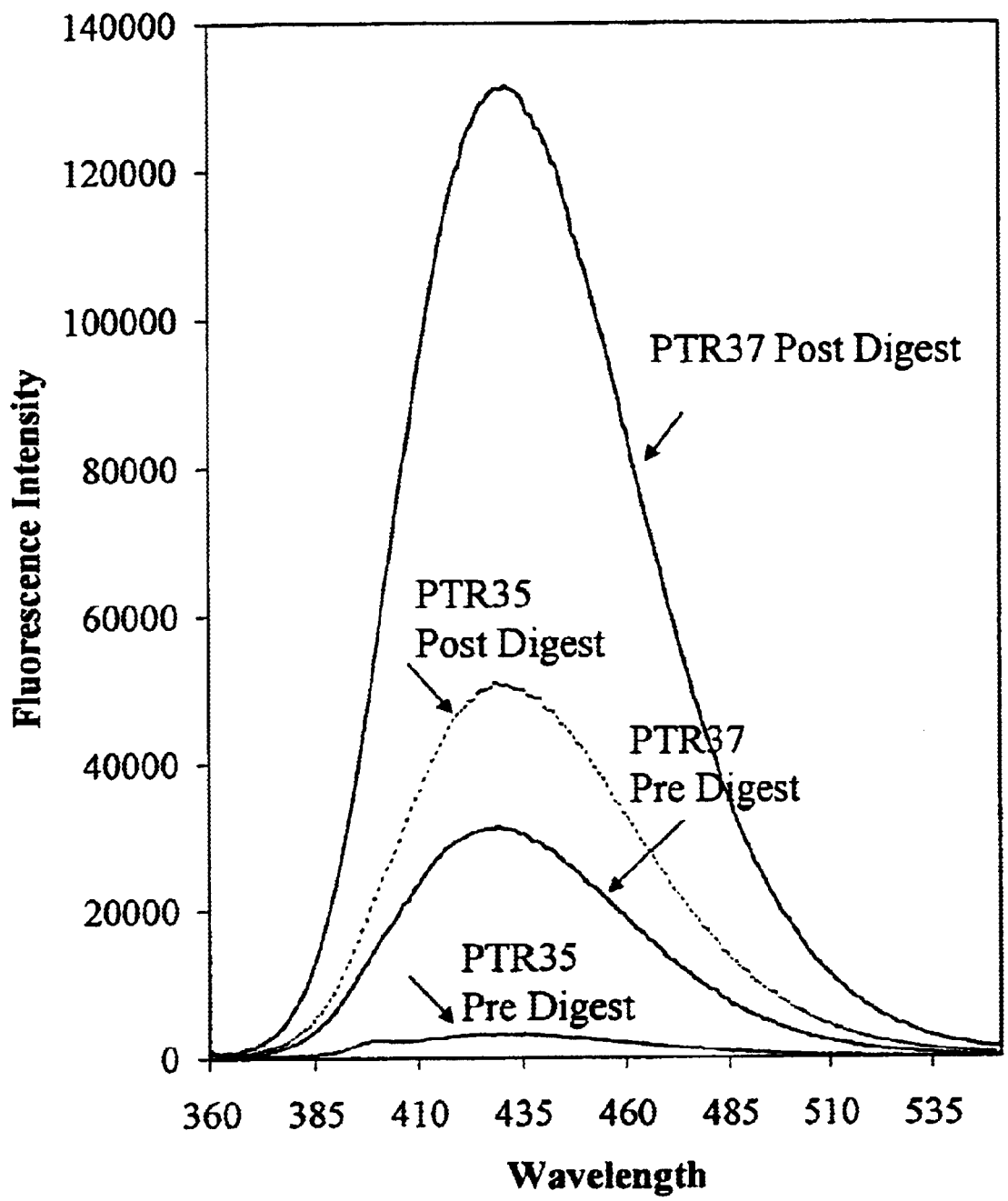
FIG. 5 illustrates effects of P1 nuclease digestion on oligonucleotides containing DMAP. Reaction mixtures were incubated overnight at 37° C.
Figure 6:
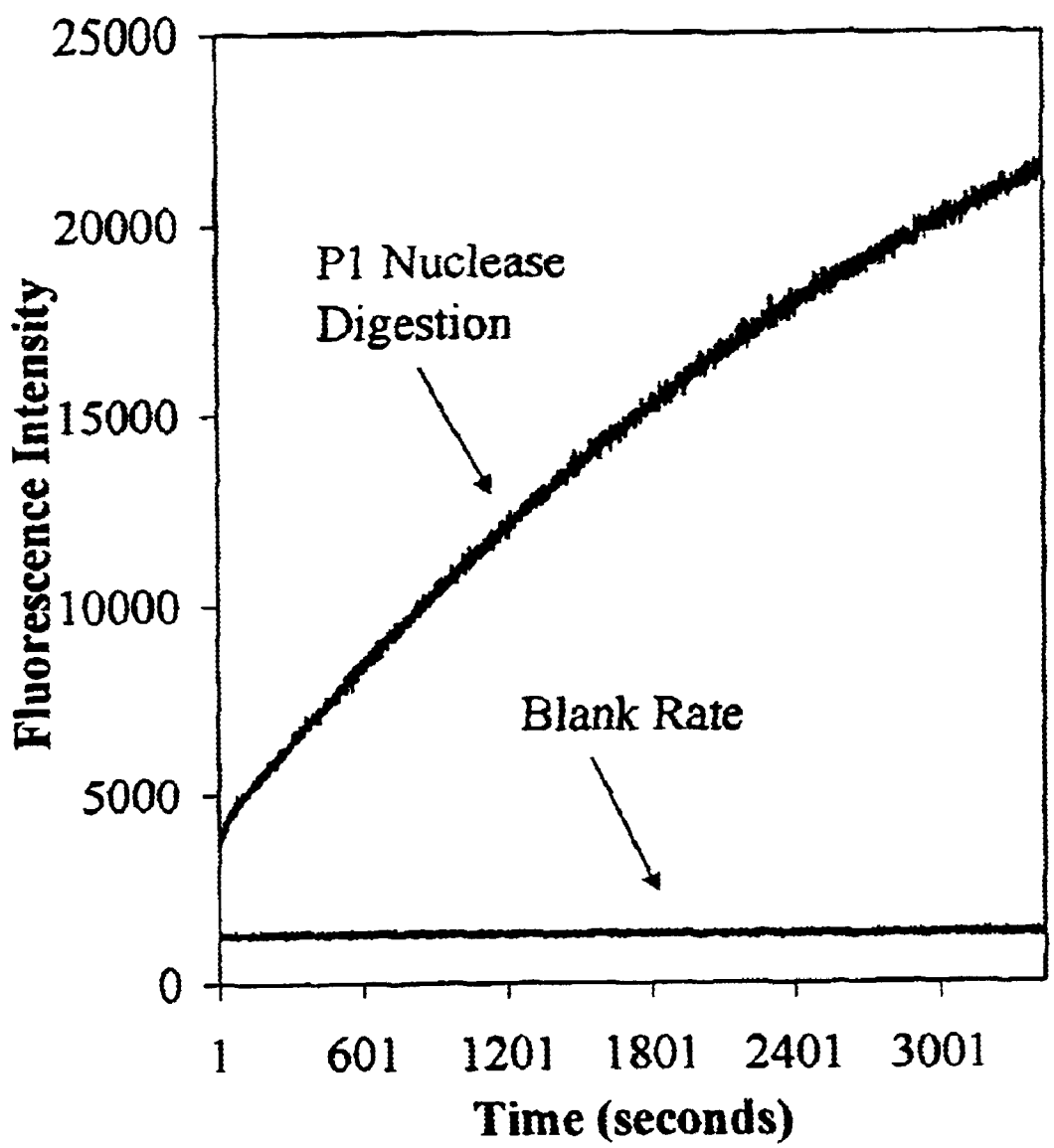
FIG. 6 illustrates P1 nuclease digestion as it occurs in the time-based acquisition mode. The blank rate contains all the same components with the exception of P1 nuclease.

The results as measured by fluorescence emission scan for P1 nuclease digestion of oligonucleotides containing either 6MAP or DMAP are shown in FIG. 4 and FIG. 5, respectively. Two separate strands for DMAP are compared to check the expected increase as compared to relative quantum yields for the oligonucleotide containing the fluorophore versus the relative quantum yield of the monomer form of the fluorophore. Real time data are displayed in FIG. 6.

The monomer forms of 6MAP and DMAP display monoexponential decay curves arid in most cases, incorporation into an oligonucleotide results in an increase in complexity of the decay curves requiring two and sometimes three components to achieve an acceptable fit. This increase in complexity combined with the impact of severe decreases in the $<\tau>$(43 to 78%) is an indication of the degree of association of the pteridine analogues with the DNA. For both 6MAP and DMAP, quench associated with going into an oligonucleotide is >97% and the decrease in $<\tau>$'s range from 43 to 71% for 6MAP and from 60% to 78% for DMAP. In those oligonucleotides experiencing a less severe decrease in $<\tau>$, the quenching mechanism can be attributed mostly to static interactions. In general, it appears that the DMAP probe is more subject to dynamic quenching than 6MAP is since decreases in $<\tau>$ are consistently greater.

These fluorophores, along with other fluorescent nucleoside analogues, exhibit unique properties that make them extremely valuable for measuring subtle events within DNA. They are highly fluorescent, stable and easy to use. Even though these compounds are significantly quenched when incorporated into an oligonucleotide, they are still very detectable using a standard bench top fluorometer. Additionally, placing one strategically within a strand of DNA gives a picture of events occurring close to that site as reported directly by changes in fluorescence intensity, anisotropy, energy transfer, or lifetime measurements experienced by the probe.

All publications, patents and patent applications mentioned in this specification are herein incorporated by reference into the specification in their entirety for all purposes. Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. An oligonucleotide comprising one or more nucleotide monomers, said monomers having the formula

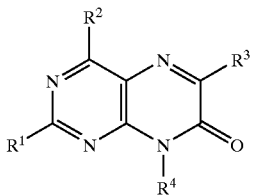

wherein:

$R^1$ is a member selected from the group consisting of hydrogen and optionally substituted $C_1$–$C_6$-alkyl;

$R^2$ is a member selected from the group consisting of amino and mono- or di-substituted amino wherein the substituent is a protecting group;

$R^3$ is optionally substituted $C_1$–$C_6$ alkyl;

$R^4$ is L;

L is of the formula

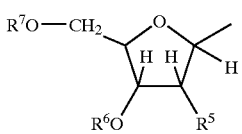

wherein:

$R^5$ is a member selected from the group consisting of hydrogen and hydroxyl;

$R^6$ is a member selected from the group consisting of hydrogen, a phosphate, a phosphate covalently attached to a nucleotide, a phosphate covalently attached to a nucleoside; a hemisuccinate covalently bound to a solid support, a dicyclohexylcarbodiimide covalently bound to a solid support, and a hydroxyalkyl covalently bound to a solid support; and $R^7$ is a member selected from the group consisting of hydrogen, a phosphate, a phosphate covalently attached to a nucleotide and a phosphate covalently attached to a nucleside;

wherein at least one of $R^6$ and $R^7$ is a phosphate covalently attached to adenosine.

2. An oligonucleotide in accordance with claim 1, wherein:

$R^1$ is hydrogen;

$R^2$ is amino;

$R^3$ is methyl;

$R^5$ is hydrogen and hydroxyl;

$R^6$ is hydrogen; and $R^7$ is a phosphate covalently attached to adenosine.

3. An oligonucleotide in accordance with claim 2, wherein:

$R^5$ is hydrogen.

4. An oligonucleotide in accordance with claim 2 wherein:

$R^5$ is hydroxyl.

5. An oligonucleotide in accordance with claim 1, wherein:

$R^1$ is optionally substituted $C_1$–$C_6$-alkyl;

$R^2$ is amino;

$R^3$ is methyl;

$R^5$ is hydrogen and hydroxyl;

$R^6$ is hydrogen; and $R^7$ is a phosphate covalently attached to adenosine.

6. An oligonucleotide in accordance with claim 5, wherein $R^1$ is methyl; and $R^5$ is hydrogen.

7. An oligonucleotide in accordance with claim 5, wherein $R^1$ is methyl; and $R^5$ is hydroxyl.

8. An oligonucleotide in accordance with claim 1, wherein said nucleotide monomers are at the 3' end of said oligonucleotide.

9. An oligonucleotide in accordance with claim 1, wherein said nucleotide monomers are at the 5' end of said oligonucleotide.

10. An oligonucleotide in accordance with claim 1, wherein said nucleotide monomers are surrounded by 1 to 10 pyrimidine monomers.

11. An oligonucleotide in accordance with claim 1, wherein said oligonucleotide is a member selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21 and SEQ ID NO:22.

12. A method of detecting the presence, absence, or quantity of a target nucleic acid, said method comprising the steps of:

a) contacting said target nucleic acid with a nucleic acid probe wherein said nucleic acid probe comprises compound of the formula.

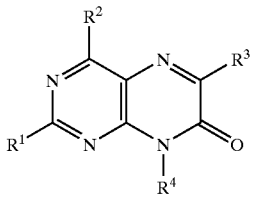

wherein:
$R^1$ is a member selected from the group consisting of hydrogen and optionally substituted $C_1$–$C_6$-alkyl;
$R^2$ is a member selected from the group consisting of amino and mono- or di-substituted amino wherein the substituent is a protecting group;
$R^3$ is optionally substituted $C_1$–$C_6$ alkyl;
$R^4$ is L;
L is of the formula

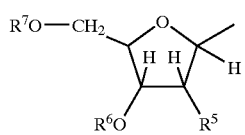

wherein:
$R^5$ is a member selected from the group consisting of hydrogen and hydroxyl;
$R^6$ is a member selected from the group consisting of hydrogen, phosphoramidite, an H-phosphonate, a methyl phosphonate, a phosphorothioate, a phosphotriester, a hemisuccinate, a hemisuccinate covalently bound to a solid support, a dicyclohexylcarbodiimide, and a dicyclohexylcarbodiimide covalently bound to a solid support; and
$R^7$ is a member selected from the group consisting of a phosphate covalently attached to a nucleotide and a phosphate covalently attached to a nucleoside;
wherein, at least one of $R^6$ and $R^7$ is a phosphate covalently attached to adenosine;
located in said probe such that, when said probe hybridizes to said target nucleic acid said compound is in a loop that does not participate in complementary base pairing with a nucleotide of said target nucleic acid; and
b) detecting the fluorescence produced by said fluorescent nucleotide when said probe forms a hybrid duplex with said target nucleic acid.

13. A method of claim 12, wherein said loop ranges in length from about 1 to about 100 nucleotides when said probe hybridizes to said target nucleic acid.

14. A method of claim 12, wherein said loop is an insertion in said nucleic acid probe which is otherwise complementary to said target nucleic acid or to a contiguous subsequence of said target nucleic acid.

15. A method of claim 14, wherein said insertion is three nucleotides in length and comprises two nucleotides each adjacent to said compound.

16. A method of claim 15, wherein at least one nucleotide adjacent to said compound is a purine.

17. A method of claim 16, wherein at least one nucleotide adjacent to said compound is an adenosine.

18. A method of claim 15, wherein at least one nucleotide adjacent to said compound is a pyrimidine.

19. A method of claim 18, wherein at least one nucleotide adjacent to said compound is a cytosine.

20. A method of claim 17, wherein said compound is bordered by at least two adjacent purines in both the 5' and 3' direction.

21. A method of claim 20, wherein said adjacent purines are adenosine.

22. A method of claim 14, wherein said insertion is said compound.

23. A method of claim 14, wherein said insertion is self-complementary and forms a hairpin wherein said compound is present in the loop of said hairpin and does not participate in complementary base pairing.

24. A method of claim 12, wherein the nucleotides comprising said loop are selected such that they are not complementary to the corresponding nucleotides of the target nucleic acid when said probe is hybridized to said target nucleic acid and wherein said probe is complementary to at least two non-contiguous subsequences of said target nucleic acid.

25. A method of claim 12, wherein said fluorescent nucleotide is present in a terminal subsequence of said nucleic acid probe wherein said terminal subsequence does not hybridize to said target nucleic acid when the remainder of said nucleic acid probe hybridizes to said target nucleic acid.

26. A method of claim 25, wherein said terminal subsequence forms a terminal hairpin by hybridization with a second subsequence of said probe such that said fluorescent nucleotide is present in a loop of said hairpin and does not participate in complementary base pairing.

27. A method of claim 12, wherein said detecting comprises detecting an increase in fluorescence of said fluorescent nucleotide when said probe forms a hybrid duplex with said target nucleic acid.

28. An oligonucleotide in accordance with claim 1 wherein $R^6$ and $R^7$ are both adenosine.

29. An oligonucleotide in accordance with claim 28 wherein an adenosine is next to $R^6$ and an adenosine is next to $R^7$.

30. A kit for the detection of nucleic acid-nucleic acid interactions comprising instructions for use, and a container, said container containing a compound of the formula:

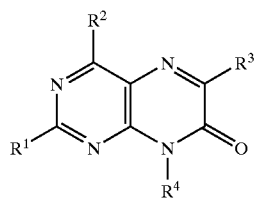

wherein:

$R^1$ is a member selected from the group consisting of hydrogen and optionally substituted $C_1$–$C_6$-alkyl;

$R^2$ is a member selected from the group consisting of amino and mono- or di-substituted amino wherein the substituent is a protecting group;

$R^3$ is optionally substituted $C_1$–$C_6$ alkyl;

$R^4$ is L;

L is of the formula

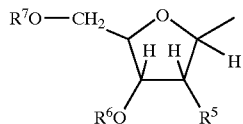

wherein:

$R^5$ is hydroxyl;

$R^6$ is a member selected from the group consisting of hydrogen, phosphoramidite, an H-phosphonate, a methyl phosphonate, a phosphorothioate, a phosphotriester, a hemisuccinate, a hemisuccinate covalently bound to a solid support, a dicyclohexylcarbodiimide, and a dicyclohexylcarbodiimide covalently bound to a solid support, a hydroxyalkyl, and a hydroxyalkyl covalently bound to a solid support; and $R^7$ is a member selected from the group consisting of hydrogen, a phosphate, a triphosphate, and a protecting group.

* * * * *

SEQUENCE LISTING

```
<160> NUMBER OF SEQ ID NOS: 22

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:
      oligonucleotide PTR21
<220> FEATURE:
<221> NAME/KEY: modified_base
<222> LOCATION: (7)
```

```
<223> OTHER INFORMATION: n = 4-amino-6-methyl-8-[-2-deoxy-5-O-(4,4'-
      dimethoxytrityl)-beta-D-ribofuranosyl]-7(8H)-pteridone-3'-O-(H-
      beta-cyanoethyl N-diisopropyl)phosphoramidite (6MAP, compound 11)

<400> SEQUENCE: 1
gtgtggnaaa tctctagcag t                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:
      oligonucleotide PTR22
<220> FEATURE:
<221> NAME/KEY: modified_base
<222> LOCATION: (10)
<223> OTHER INFORMATION: n = 4-amino-6-methyl-8-[-2-deoxy-5-O-(4,4'-
      dimethoxytrityl)-beta-D-ribofuranosyl]-7(8H)-pteridone-3'-O-(H-
      beta-cyanoethyl N-diisopropyl)phosphoramidite (6MAP, compound 11)

<400> SEQUENCE: 2
gtgtggaaan tctctagcag t                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:
      oligonucleotide PTR23
<220> FEATURE:
<221> NAME/KEY: modified_base
<222> LOCATION: (16)
<223> OTHER INFORMATION: n = 4-amino-6-methyl-8-[-2-deoxy-5-O-(4,4'-
      dimethoxytrityl)-beta-D-ribofuranosyl]-7(8H)-pteridone-3'-O-(H-
      beta-cyanoethyl N-diisopropyl)phosphoramidite (6MAP, compound 11)

<400> SEQUENCE: 3
gtgtggaaaa tctctngcag t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:
      oligonucleotide PTR24
<220> FEATURE:
<221> NAME/KEY: modified_base
<222> LOCATION: (7)
<223> OTHER INFORMATION: n = 4-amino-6-methyl-8-[-2-deoxy-5-O-(4,4'-
      dimethoxytrityl)-beta-D-ribofuranosyl]-7(8H)-pteridone-3'-O-(H-
      beta-cyanoethyl N-diisopropyl)phosphoramidite (6MAP, compound 11)

<400> SEQUENCE: 4
actgctngag attttccaca c                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:
      oligonucleotide PTR25
<220> FEATURE:
<221> NAME/KEY: modified_base
<222> LOCATION: (9)
<223> OTHER INFORMATION: n = 4-amino-6-methyl-8-[-2-deoxy-5-O-(4,4'-
      dimethoxytrityl)-beta-D-ribofuranosyl]-7(8H)-pteridone-3'-O-(H-
      beta-cyanoethyl N-diisopropyl)phosphoramidite (6MAP, compound 11)
```

<400> SEQUENCE: 5
actgctagng attttccaca c     21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:
      oligonucleotide PTR28
<220> FEATURE:
<221> NAME/KEY: modified_base
<222> LOCATION: (11)
<223> OTHER INFORMATION: n = 4-amino-6-methyl-8-[-2-deoxy-5-O-(4,4'-
      dimethoxytrityl)-beta-D-ribofuranosyl]-7(8H)-pteridone-3'-O-(H-
      beta-cyanoethyl N-diisopropyl)phosphoramidite (6MAP, compound 11)

<400> SEQUENCE: 6
actgctagcc nttttccaca c     21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:
      oligonucleotide HP21
<220> FEATURE:
<221> NAME/KEY: modified_base
<222> LOCATION: (10)
<223> OTHER INFORMATION: n = 4-amino-6-methyl-8-[-2-deoxy-5-O-(4,4'-
      dimethoxytrityl)-beta-D-ribofuranosyl]-7(8H)-pteridone-3'-O-(H-
      beta-cyanoethyl N-diisopropyl)phosphoramidite (6MAP, compound 11)

<400> SEQUENCE: 7
attccacaan gccgtgtca     19

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:
      oligonucleotide HP22
<220> FEATURE:
<221> NAME/KEY: modified_base
<222> LOCATION: (11)
<223> OTHER INFORMATION: n = 4-amino-6-methyl-8-[-2-deoxy-5-O-(4,4'-
      dimethoxytrityl)-beta-D-ribofuranosyl]-7(8H)-pteridone-3'-O-(H-
      beta-cyanoethyl N-diisopropyl)phosphoramidite (6MAP, compound 11)

<400> SEQUENCE: 8
agaggtgtcc ncctgtggag a     21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:
      oligonucleotide HP23
<220> FEATURE:
<221> NAME/KEY: modified_base
<222> LOCATION: (11)
<223> OTHER INFORMATION: n = 4-amino-6-methyl-8-[-2-deoxy-5-O-(4,4'-
      dimethoxytrityl)-beta-D-ribofuranosyl]-7(8H)-pteridone-3'-O-(H-
      beta-cyanoethyl N-diisopropyl)phosphoramidite (6MAP, compound 11)

<400> SEQUENCE: 9
agaggtgtac nagtgtggag a                    21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:
    oligonucleotide HP24
<220> FEATURE:
<221> NAME/KEY: modified_base
<222> LOCATION: (11)
<223> OTHER INFORMATION: n = 4-amino-6-methyl-8-[-2-deoxy-5-O-(4,4'-
    dimethoxytrityl)-beta-D-ribofuranosyl]-7(8H)-pteridone-3'-O-(H-
    beta-cyanoethyl N-diisopropyl)phosphoramidite (6MAP, compound 11)

<400> SEQUENCE: 10
agaggtgtaa naatgtggag a                    21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence:
    oligonucleotide PTR31
<220> FEATURE:
<221> NAME/KEY: modified_base
<222> LOCATION: (7)
<223> OTHER INFORMATION: n = 4-amino-2,6-dimethyl-8-[-2-deoxy-5-O-(4,4'-
    dimethoxytrityl)-beta-D-ribofuranosyl]-7(8H)-pteridone-3'-O-(H-
    beta-cyanoethyl N-diisopropyl)phosphoramidite (DMAP, compound 12)

<400> SEQUENCE: 11
gtgtggnaaa tctctagcag t                    21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:
    oligonucleotide PTR32
<220> FEATURE:
<221> NAME/KEY: modified_base
<222> LOCATION: (10)
<223> OTHER INFORMATION: n = 4-amino-2,6-dimethyl-8-[-2-deoxy-5-O-(4,4'-
    dimethoxytrityl)-beta-D-ribofuranosyl]-7(8H)-pteridone-3'-O-(H-
    beta-cyanoethyl N-diisopropyl)phosphoramidite (DMAP, compound 12)

<400> SEQUENCE: 12
gtgtggaaan tctctagcag t                    21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:
    oligonucleotide PTR33
<220> FEATURE:
<221> NAME/KEY: modified_base
<222> LOCATION: (16)
<223> OTHER INFORMATION: n = 4-amino-2,6-dimethyl-8-[-2-deoxy-5-O-(4,4'-
    dimethoxytrityl)-beta-D-ribofuranosyl]-7(8H)-pteridone-3'-O-(H-
    beta-cyanoethyl N-diisopropyl)phosphoramidite (DMAP, compound 12)

<400> SEQUENCE: 13
gtgtggaaaa tctctngcag t                    21

```
<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:
      oligonucleotide PTR34
<220> FEATURE:
<221> NAME/KEY: modified_base
<222> LOCATION: (7)
<223> OTHER INFORMATION: n = 4-amino-2,6-dimethyl-8-[-2-deoxy-5-O-(4,4'-
      dimethoxytrityl)-beta-D-ribofuranosyl]-7(8H)-pteridone-3'-O-(H-
      beta-cyanoethyl N-diisopropyl)phosphoramidite (DMAP, compound 12)

<400> SEQUENCE: 14
actgctngag attttccaca c                                          21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence:
      oligonucleotide PTR35
<220> FEATURE:
<221> NAME/KEY: modified_base
<222> LOCATION: (9)
<223> OTHER INFORMATION: n = 4-amino-2,6-dimethyl-8-[-2-deoxy-5-O-(4,4'-
      dimethoxytrityl)-beta-D-ribofuranosyl]-7(8H)-pteridone-3'-O-(H-
      beta-cyanoethyl N-diisopropyl)phosphoramidite (DMAP, compound 12)

<400> SEQUENCE: 15
actgctagng attttccaca c                                          21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:
      oligonucleotide PTR36
<220> FEATURE:
<221> NAME/KEY: modified_base
<222> LOCATION: (11)
<223> OTHER INFORMATION: n = 4-amino-2,6-dimethyl-8-[-2-deoxy-5-O-(4,4'-
      dimethoxytrityl)-beta-D-ribofuranosyl]-7(8H)-pteridone-3'-O-(H-
      beta-cyanoethyl N-diisopropyl)phosphoramidite (DMAP, compound 12)

<400> SEQUENCE: 16
actgctagag ntttccaca c                                           21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:
      oligonucleotide PTR37
<220> FEATURE:
<221> NAME/KEY: modified_base
<222> LOCATION: (18)
<223> OTHER INFORMATION: n = 4-amino-2,6-dimethyl-8-[-2-deoxy-5-O-(4,4'-
      dimethoxytrityl)-beta-D-ribofuranosyl]-7(8H)-pteridone-3'-O-(H-
      beta-cyanoethyl N-diisopropyl)phosphoramidite (DMAP, compound 12)

<400> SEQUENCE: 17
actgctagag attttccnca c                                          21

<210> SEQ ID NO 18
<211> LENGTH: 21
<212> TYPE: DNA
```

```
<213> ORGANISM: Artificial Sequence
<220> FEATURE:
<223> OTHER INFORMATION: Description of Artificial Sequence:
      oligonucleotide PTR38
<220> FEATURE:
<221> NAME/KEY: modified_base
<222> LOCATION: (11)
<223> OTHER INFORMATION: n = 4-amino-2,6-dimethyl-8-[-2-deoxy-5-O-(4,4'-
      dimethoxytrityl)-beta-D-ribofuranosyl]-7(8H)-pteridone-3'-O-(H-
      beta-cyanoethyl N-diisopropyl)phosphoramidite (DMAP, compound 12)

<400> SEQUENCE: 18
actgctagcc nttttccaca c                                              21

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence:
      oligonucleotide HP31
<220> FEATURE:
<221> NAME/KEY: modified_base
<222> LOCATION: (10)
<223> OTHER INFORMATION: n = 4-amino-2,6-dimethyl-8-[-2-deoxy-5-O-(4,4'-
      dimethoxytrityl)-beta-D-ribofuranosyl]-7(8H)-pteridone-3'-O-(H-
      beta-cyanoethyl N-diisopropyl)phosphoramidite (DMAP, compound 12)

<400> SEQUENCE: 19
attccacaan gccgtgtca                                                 19

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:
      oligonucleotide HP32
<220> FEATURE:
<221> NAME/KEY: modified_base
<222> LOCATION: (11)
<223> OTHER INFORMATION: n = 4-amino-2,6-dimethyl-8-[-2-deoxy-5-O-(4,4'-
      dimethoxytrityl)-beta-D-ribofuranosyl]-7(8H)-pteridone-3'-O-(H-
      beta-cyanoethyl N-diisopropyl)phosphoramidite (DMAP, compound 12)

<400> SEQUENCE: 20
agaggtgtcc ncctgtggag a                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence:
      oligonucleotide HP33
<220> FEATURE:
<221> NAME/KEY: modified_base
<222> LOCATION: (11)
<223> OTHER INFORMATION: n = 4-amino-2,6-dimethyl-8-[-2-deoxy-5-O-(4,4'-
      dimethoxytrityl)-beta-D-ribofuranosyl]-7(8H)-pteridone-3'-O-(H-
      beta-cyanoethyl N-diisopropyl)phosphoramidite (DMAP, compound 12)

<400> SEQUENCE: 21
agaggtgtac nagtgtggag a                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence:
```

```
       oligonucleotide HP34
<220> FEATURE:
<221> NAME/KEY: modified_base
<222> LOCATION: (11)
<223> OTHER INFORMATION: n = 4-amino-2,6-dimethyl-8-[-2-deoxy-5-O-(4,4'-
      dimethoxytrityl)-beta-D-ribofuranosyl]-7(8H)-pteridone-3'-O-(H-
      beta-cyanoethyl N-diisopropyl)phosphoramidite (DMAP, compound 12)

<400> SEQUENCE: 22
agaggtgtaa naatgtggag a                                              21
```